(12) United States Patent
Hagiwara et al.

(10) Patent No.: US 9,243,013 B2
(45) Date of Patent: Jan. 26, 2016

(54) IONIC COMPOUND, METHOD FOR PRODUCING THE SAME, AND ION-CONDUCTIVE MATERIAL COMPRISING THE SAME

(75) Inventors: Yuji Hagiwara, Isumi (JP); Takanori Ochi, Isumi (JP); Kazunobu Ohata, Isumi (JP); Taisuke Kasahara, Suita (JP); Taketo Toba, Takarazuka (JP); Keiichiro Mizuta, Akashi (JP); Hiromoto Katsuyama, Shimamoto-cho (JP); Satoshi Ishida, Kyoto (JP); Toshifumi Nishida, Osaka (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 13/060,161

(22) PCT Filed: Aug. 21, 2009

(86) PCT No.: PCT/JP2009/064678
§ 371 (c)(1),
(2), (4) Date: Feb. 22, 2011

(87) PCT Pub. No.: WO2010/021391
PCT Pub. Date: Feb. 25, 2010

(65) Prior Publication Data
US 2011/0150736 A1    Jun. 23, 2011

(30) Foreign Application Priority Data

Aug. 22, 2008  (JP) ................. 2008-214504
Sep. 18, 2008  (JP) ................. 2008-240014
Mar. 9, 2009   (JP) ................. 2009-055643
May 19, 2009   (JP) ................. 2009-121465
Jun. 5, 2009   (JP) ................. 2009-136719
Jul. 24, 2009  (JP) ................. 2009-173577
Jul. 30, 2009  (JP) ................. 2009-178166
Jul. 30, 2009  (JP) ................. 2009-178167

(51) Int. Cl.
*C07F 5/02*     (2006.01)
*C07F 9/02*     (2006.01)
(Continued)

(52) U.S. Cl.
CPC .......... *C07F 9/65688* (2013.01); *C07D 233/58* (2013.01); *C07F 5/02* (2013.01); *C07F 5/022* (2013.01); *H01B 1/122* (2013.01)

(58) Field of Classification Search
None
See application file for complete search history.

(56) References Cited

U.S. PATENT DOCUMENTS 7,914,927 B2    3/2011  Mizuta et al.
2002/0090547 A1  7/2002  Schmidt et al.
(Continued)

FOREIGN PATENT DOCUMENTS

CN    1358726    7/2002
CN    1751053    3/2006
(Continued)

OTHER PUBLICATIONS

Bernhardt et al., "Die Tetracyanoborate M[B(CN)$_4$], M=[Bu$_4$N]$^+$, Ag$^+$, K$^+$", Z. Anorg. Allg. Chem., 2000, vol. 626, pp. 560-568.
(Continued)

*Primary Examiner* — Clinton Brooks
(74) *Attorney, Agent, or Firm* — Wenderoth, Lind & Ponack, L.L.P.

(57) ABSTRACT

The present invention provides a method of producing a tetracyanoborate-containing ionic compound in a milder condition more efficiently and less expensively than conventional methods, and a tetracyanoborate-containing ionic compound having a reduced content of impure components. An ionic compound of the present invention is represented by the following general formula (I), has a content of fluorine atom-containing impurities of 3 mol % or less per 100 mol % of the ionic compound, and a method for producing an ionic compound represented by the general formula (I) of the present invention comprises a step of reacting starting materials containing a cyanide and a boron compound.

(I)

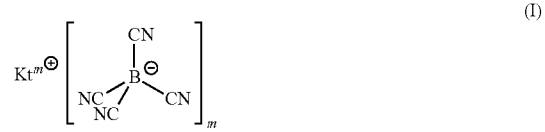

(In the formula, Kt$^{m+}$ denotes an organic cation [Kt$^b$]$^{m+}$ or an inorganic cation [Ke]$^{m+}$; and m denotes an integer of 1 to 3.)

7 Claims, 1 Drawing Sheet

(51) Int. Cl.
*C07F 9/6568* (2006.01)
*C07D 233/58* (2006.01)
*H01B 1/12* (2006.01)

(56) References Cited

U.S. PATENT DOCUMENTS

| | | | |
|---|---|---|---|
| 2004/0002002 | A1 | 1/2004 | Mizuta et al. |
| 2006/0222584 | A1 | 10/2006 | Welz-Biermann et al. |
| 2007/0293391 | A1 | 12/2007 | Finze et al. |
| 2010/0069655 | A1 | 3/2010 | Finze et al. |
| 2010/0173195 | A1 | 7/2010 | Mizuta et al. |

FOREIGN PATENT DOCUMENTS

| | | |
|---|---|---|
| JP | 8-107048 | 4/1996 |
| JP | 2000-318080 | 11/2000 |
| JP | 2002-308884 | 10/2002 |
| JP | 2003-142100 | 5/2003 |
| JP | 2004-165131 | 6/2004 |
| JP | 2004-175666 | 6/2004 |
| JP | 2005-302950 | 10/2005 |
| JP | 2006-517546 | 7/2006 |
| JP | 2008-517002 | 5/2008 |

OTHER PUBLICATIONS

Bernhardt et al., "Die Reaktionen von M[BF$_4$] (M=Li, K) und (C$_2$H$_5$)$_2$O-BF$_3$ mit (CH$_3$)$_3$SiCN, Bildung von M[BF$_x$(CN)$_{4-x}$] (M=Li, K; x=1, 2) und (CH$_3$)$_3$SiNCBF$_x$(CN)$_{3-x}$, (x=0, 1)", Z. Anorg. Allg. Chem., 2003, vol. 629, pp. 677-685.
Bernhardt et al., "Eine effiziente Synthese von Tetracyanoboraten durch Sinterprozesse", Z. Anorg. Allg. Chem., 2003, vol. 629, pp. 1229-1234.
Matar et al., "Ab initio studies of the electronic structure of the quaternary system LiBC$_4$N$_4$", J. Alloys Compd., 2007, vol. 427, pp. 61-66.
International Search Report issued Sep. 15, 2009 in corresponding International Application No. PCT/JP2009/064678, of record.
Williams et al., "Synthesis of LiBC$_4$N$_4$, BC$_3$N$_3$, and Related C-N Compounds of Boron: New Precursors to Light Element Ceramics", J. Am. Chem. Soc., 2000, vol. 122, pp. 7735-7741.
Uznanski et al., "An Improved Preparation of Trimethylsilyl Cyanide", Synthesis, 1978, pp. 154-155.
Ue et al., "Anodic Stability of Several Anions Examined by Ab Initio Molecular Orbital and Density Functional Theories", Journal of the Electrochemical Society, 2002, vol. 149(12), pp. A1572-A1577.
Bessler Von E., "Darstellung und Eigenschaften von AgB(Cn)$_4$ und CuB(CN)$_4$" aka "Preparation and Properties of AgB(CN)$_4$ and CuB(CN)$_4$", Z. Anorg. Allg. Chem., 1977, vol. 430, pp. 38-42.
Supplementary European Search Report issued Apr. 27, 2012 in corresponding European Application No. 09808327.2.
Office Action issued Oct. 22, 2013 in corresponding Japanese Application No. 2010-525722, with English translation thereof.
European Office Action issued Apr. 9, 2013 in corresponding European Application No. 09 808 327.2.
Chinese Office Action, with English translation, issued Feb. 28, 2013 in corresponding Chinese Patent Application No. 200980132280.9.
Office Action issued May 14, 2013 in corresponding Japanese Application No. 2008-240013, with English language translation thereof.
Chinese Office Action issued Dec. 25, 2013 in Application No. 200980132280.9 with its English translation.
Chinese Notice of Rejection issued Jun. 27, 2014 in corresponding Chinese Application No. 200980132280.9 (with English translation).
Notice of Reasons for Rejection mailed Jan. 7, 2014 in corresponding Japanese Application No. 2008-240013, with English translation thereof.
Decision of Rejection mailed Jan. 28, 2014 in corresponding Japanese Application No. 2010-525722, with English translation thereof.
European Office Action issued Dec. 19, 2014 in corresponding Application No. 09 808 327.2.
Notice of Release of Pretrial Reexamination issued Aug. 12, 2014 in corresponding Japanese Application No. 2010-525722 (with English translation).
Office Action issued Apr. 1, 2015 in corresponding Japanese Application No. 2014-093193 (with English translation).
Notification of Reasons for Refusal issued Aug. 11, 2015 in corresponding Japanese Patent Application No. 2010-525722, with English translation.
Decision to Dismiss the Amendment issued Aug. 18, 2015 in corresponding Japanese Patent Application No. 2010- 525722, with English translation.
Japanese Notice of Reasons for Refusal issued Nov. 10, 2015 in corresponding Japanese Patent Application No. 2010-575722 with English Translation.

IONIC COMPOUND, METHOD FOR PRODUCING THE SAME, AND ION-CONDUCTIVE MATERIAL COMPRISING THE SAME

TECHNICAL FIELD

The invention relates to an ionic compound, more particularly, an ionic compound having a tetracyanoborate anion and its production method as well as an ion-conductive material using the same, an electrolyte solution containing the same, and an electrochemical device containing the material.

BACKGROUND ART

An ionic compound has been used for an ion conductor for various kinds of battery cells based on ion conduction and has been employed for electrochemical devices such as primary batteries and batteries having charge/discharge mechanism, e.g., lithium (ion) secondary batteries and fuel cells, and also electrolytic capacitors, electric double layer capacitors, lithium ion capacitors, solar cells, electrochromic display devices, etc. In general, these electrochemical devices are each composed of a pair of electrodes and an ion conductor formed between the electrodes.

Examples of the ion conductor are electrolyte solutions and solid electrolytes and those obtained by dissolving an electrolyte in an organic solvent or a polymer compound or their mixture are used as the ion conductor. In the ion conductor, the electrolyte is dissolved and dissociated into a cation and an anion to exhibit ion conductivity. A battery using such an ion conductor has been used for portable electronic appliances such as lap-top type and palmtop type computers, mobile phones, video cameras, etc., and along with wide spread of these appliances, the necessity of lightweight and powerful batteries has been increased. Further, in terms of environmental issues, the importance of development of secondary batteries with longer lives has been increased.

As an ionic compound to be used for the above-mentioned secondary batteries or the like, lithium hexafluorophosphate (LiPF$_6$) and lithium tetrafluoroborate (LiBF$_4$), which are electrolytic salts, and cyanoborates containing alkali metals and organic cations have been proposed. An ionic compound containing the above-mentioned cyanoborate as an anionic component has a characteristic as an ionic liquid, that is, the ionic compound is a liquid even at room temperature and shows a characteristic of being thermally, physically, and also electrochemically stable and thus has been investigated for applications to various uses.

There have been proposed various methods to synthesize a compound containing tetracyanoborate (TCB:[B(CN)$_4$]$^-$) among the above-mentioned cyanoborates; that is, a method of reacting a compound containing boron and an alkali metal cyanide (Z. Anorg. Allg. Chem. 2000, vol. 626, p. 560-568), a method of carrying out the above-mentioned reaction in the presence of a lithium halide such as LiCl or the like (Japanese Patent Application Publication (Translation of PCT Application) No. 2006-517546), a method of reacting a boron compound such as KBF$_4$, LiBF$_4$, and BF$_3$.OEt$_2$ with trimethylsilyl cyanide (Z. Anorg. Allg. Chem. 2003, vol. 629, p 677-685, H. Willner, et al., (two others), Z. Anorg, Allg. Chem. 2003, 629, p 1229-1234, J. Alloys Compd. 2007. 427. p 61-66, R. A. Andersen, et al. (four others), JACS. 2000. 122. p 7735-7741), etc.

DISCLOSURE OF THE INVENTION

Problems to be Solved by the Invention

However, since an alkali metal cyanide has low reactivity with a boron compound, it is needed to carry out the reaction under high temperature condition around 300° C. or to use an excess amount of the alkali metal cyanide and thus there are problems that it costs a high installation cost to introduce facilities with such high durability as to deal with the above-mentioned reaction condition and that impurities are easy to be produced. On the other hand, there are also problems that trimethylsilyl cyanide is expensive: the yield of the product is low: and that a salt of tetracyanoborate and trimethylsilane is instable and easy to be decomposed by heating.

In this connection, a method of synthesizing tetrabutylammonium tetracyanoborate (Bu$_4$NB(CN)$_4$) by using [NBu$_4$]X, BX$_3$ (X=Br, Cl), and KCN is reported in Z. Anorg. Allg. Chem. 2000, vol. 626, p. 560-568; however it is difficult to synthesize the above-mentioned compound by a check experiment under the condition described in the above-mentioned Document and accordingly, a method of more stably obtaining a tetracyanoborate-containing compound has been required.

Further, in the case an ionic compound is to be used for electrochemical devices as described above, from a viewpoint of reliably attaining good ion conductivity and preventing corrosion or the like of peripheral members, it is required to lower impure ionic components contained in the ionic compound. For example, in the case the cyanoborate anion-containing compound described in the above-mentioned Document is used as an electrolyte of an electrolyte solution of the above-mentioned electrochemical devices, it is particularly indispensable to lower cyanide ion (CN$^-$), halide ion, and metal ion.

However, in almost all of the conventionally employed methods, fluorine-containing boron compounds are usually used as raw materials. Particularly, in the case of synthesis of a compound containing cyanoborate as an anion, a starting material sometimes remains, or isolated CN$^-$ and water sometimes remain in the compound and in such a case, heat resistance of the ionic compound is lowered in some cases. Furthermore, these impurities remaining in the electrolyte lower the ionic conduction capability and corrode the peripheral members such as electrodes, resulting in a cause of deterioration of the electrochemical capability.

In view of the above state of the art, it is an object of the invention to provide a method of producing a tetracyanoborate-containing ionic compound in a milder condition more efficiently and less expensively than conventional methods and a tetracyanoborate-containing ionic compound with a reduced content of impure components.

Solution to the Problems

The ionic compound of the present invention which has solved the above-mentioned problems is an ionic compound represented by the following general formula (I), has content of fluorine atom-containing impurities of 3 mol % or less per 100 mol % of the ionic compound:

[Chemical Formula 1]

(wherein, Kt$^{m+}$ denotes an organic cation [Kt$^b$]$^{m+}$ or an inorganic cation [Kt$^a$]$^{m+}$; and m denotes an integer of 1 to 3.)

Since the ionic compound of the invention has content of impurities containing fuluorine atom (F atom) being lowered to an extremely low level, deterioration of the ionic compound properties derived from F atom and F atom-containing impurity, which are originated from the starting materials, is hardly caused.

Further, it is preferable that the ionic compound has silicon content of 2500 ppm or lower in the ionic compound. Furthermore, CN⁻ content is preferable to be 3000 ppm or lower; halide ion content is preferable to be 500 ppm or lower; and additionally water content is preferable to be 3000 ppm or lower.

An ion-conductive material containing the above-mentioned ionic compound is one of the preferable embodiments of the present invention.

A production method of the present invention is a method for producing an ionic compound represented by the general formula (I), which comprises a step of reacting starting materials containing a cyanide and a boron compound.

The production method of the present invention includes a method employing the starting materials containing trimethylsilyl cyanide as the cyanide and further an amine and/or ammonium salt; a method and; a method employing the starting materials containing, as the cyanide, $M^a(CN)_n$ ($M^a$ denotes any of $Zn^{2+}$, $Ga^{3+}$, $Pd^{2+}$, $Sn^{2+}$, $Hg^{2+}$, $Rh^{2+}$, $Cu^{2+}$, and $Pb^+$; and n is an integer of 1 to 3); a method employing the starting materials containing, as the cyanide, an ammonium cyanide type compound represented as $R_4NCN$ (wherein R denotes H or an organic group) and; a method employing the starting materials containing hydrogen cyanide as the cyanide and further containing an amine compound.

According to these production method, an ionic compound represented by the above-mentioned general formula (I) is produced in a milder condition, or more efficiently.

It is preferable that the production method of the present invention further comprises a step of bringing a crude product, which was obtained by reacting the starting materials, into contact with an oxidizing agent. Furthermore, hydrogen peroxide is preferable as the oxidizing agent.

Effects of the Invention

According to the production method of the present invention, an ionic compound containing a tetracyanoborate ion ($[B(CN)_4]^-$) can be produced in a milder condition, or more efficiently, or less expensively than conventional methods. Consequently, it is made possible to industrially produce the ionic compound of the invention.

Since the ionic compound of the invention has a wide potential window and a content of impurities lowered to an extremely low level, even in a case of using the ionic compound for various kinds of uses such as electrolyte solutions and electrochemical devices, stable characteristics (thermal, physical, electrochemical characteristics, etc.) can be exerted without causing problems such as corrosion of peripheral members.

MODE FOR CARRYING OUT THE INVENTION

<Ionic Compound>

Figure 1:
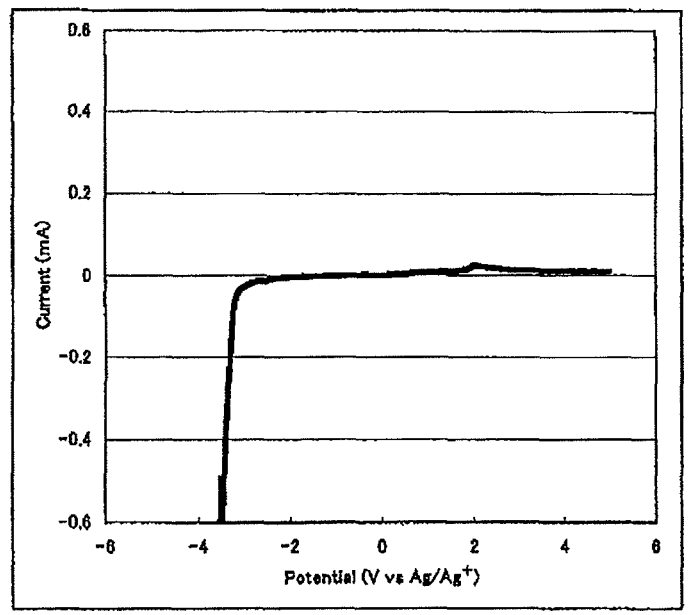
FIG. 1. A drawing showing LSV measurement result of Experiment Example 6-1.

The ionic compound of the invention is an ionic compound defined by the following general formula (I) and character-ized in that the content of fluorine atom-containing impurity is 3 mol % or less per 100 mol % of the ionic compound.

[Chemical Formula 2]

(wherein, $[Kt]^{m+}$ denotes an inorganic cation $[Kt^a]^{m+}$ or an organic cation $[Kt^b]^{m+}$; and m denotes an integer of 1 to 3).

Inventors of the present invention have made investigations on characteristics of an ionic compound such as heat resistance and electrochemical characteristics to find that the amount of impurities derived from F atoms gets significantly engaged in deterioration of the characteristics of the ionic compound and have made further investigations on an ionic compound which hardly causes such characteristic deterioration, consequently finding that if the content of F atom-containing impurity is 3 mol % or lower per 100 mol % of the ionic compound, the excellent characteristics of the ionic compound containing tetracyanoborate ion as an anion can be obtained sufficiently and the finding has now led to completion of the invention.

In the invention, the F atom-containing impurity includes all of those which contain F atoms such as free F atoms derived from the starting materials for the above-mentioned ionic compound, $BF_x(CN)_{4-x}$ (x denotes an integer of 1 to 3) which is produced as a byproduct at the time of synthesizing the above-mentioned ionic compound as well as compounds containing $BF_3$ and $BF_4$ anions, etc. It is preferable that these impurities are not contained in the ionic compound, an aimed compound: and especially, it is more preferable that free F atoms and a group of compounds having B—F bonds are not contained. Particularly, it is furthermore preferable that the compounds having B—F bonds are not contained in the ionic compound of the invention. Since the compounds having B—F bonds are reacted with water in the air and decomposed, if such compounds are contained in the ionic compound of the invention, it may result in decrease of the heat resistance and also it may cause a problem of corrosion of the peripheral members by hydrogen fluoride generated at the time of decomposition of the B—F bonds.

In the case that the ionic compound contains 3 mol % or more of the impurity such as F atom and the above-mentioned F atom-containing impurities, hydrogen fluoride gas may be generated to corrode the peripheral members of various kinds of electrochemical devices or, the characteristics (heat resistance and electric characteristics) of the ionic compound itself may be deteriorated attributed to these impurities. Accordingly, the content of the F atom-containing impurity contained in the ionic compound of the invention is more preferable as it is less, and it is preferable to be 1 mol % or less per 100 mol % of the ionic compound and more preferable to be 0.1 mol % or less. It is most preferable that the F atom-containing impurity is not contained (0 mol %) in the ionic compound of the invention; however, if the amount of the F atom-containing impurity is 0.0001 mol % or more, the effect on the characteristics of the ionic compound is little and significant deterioration of the characteristics is scarcely observed even if it is 0.001 mol % or more.

The content of the impurities contained in the ionic compound of the invention may be calculated by, for example, NMR spectrum. Concretely, at first, $^{11}B$—NMR spectrum of the ionic compound of the invention is measured. Next, the value of integral of the peak of $B(CN)_4$, which is an aimed compound, is defined as 100 mol % and compared with the value of integral of the peaks of impurities having B—F bonds to calculate the content of the impurities. Further, if $^{19}$F-NMR spectrum is measured in the same manner, the content of free F atoms and F-containing compounds can be measured. In this connection, the calculation method of the content of the impurities is not limited to the above-mentioned methods and other methods may be employed. For example, it is also possible to quantitatively measure the ion species containing F atoms and free F atoms by ion chromatography. Therefore, the method may include a method by determining the number of moles of the B(CN)$_4$ compound from the total weight of the ionic compound, calculating the weight of contained F anion by ion chromatography, and calculating the content of the impurities by conversion of the weight into the number of moles.

The ionic compound of the invention defined by the above-mentioned general formula (I) is a compound defined by the above-mentioned general formula (I) and obtained by reaction of trimethylsilyl cyanide (TMSCN) and a boron compound, and the ionic compound of the invention is preferable to be a highly pure ionic compound with content of silicon (Si) of 2500 ppm or less in the ionic compound.

Si contained in the ionic compound is derived from the starting materials at the time of synthesizing the ionic compound (reference to a production method of the invention described later). In the case such impure components are contained, if the compound is used for an electrolyte solution or the like, the ion conductivity may be lowered in some cases. Therefore, it is desirable to lower and remove the impure components as much as possible. Consequently, the Si content in the ionic compound is more preferably 1000 ppm or less and furthermore preferably 500 ppm or less.

Further, the high purity ionic compound of the invention is preferable to have low content of cyanide ion (CN$^-$) in addition to the above-mentioned Si. The content of the cyanide ion is preferably 3000 ppm or less. The cyanide ion may possibly lower the ion conductivity by reaction with electrodes. The content of the cyanide ion is more preferably 1000 ppm or less and even more preferably 500 ppm or less.

Moreover, the high purity ionic compound of the invention is preferable to have a low content of a halide ion in addition to the above-mentioned Si and cyanide ion. Herein, "the content of a halide ion" means the total of the concentrations of the respective halide ions of F$^-$, Cl$^-$, Br$^-$, and I$^-$. As described above, halide ions are reacted with electrode materials and corrode the electrode materials and further, in the case hydrogen ion exists in a system, halide ions may possibly lower the pH of the electrolyte solution and dissolve the electrode materials and deteriorate the capability of electrochemical devices in any case.

Consequently, the halide ion amount in the ionic compound is more preferable as it is less and the content of the halide ions in the ionic compound is preferably 500 ppm or less, more preferably 100 ppm or less, and furthermore preferably 30 ppm or less. Among the halide ions of F$^-$, Cl$^-$, Br$^-$, and I$^-$, the content of F$^-$ and Cl$^-$ is preferably in the above-mentioned range and the content of Cl$^-$ is particularly preferably in the above-mentioned range.

In addition to the above-mentioned ionic components, the amount of water (water concentration) contained in the ionic compound of the invention is preferable to be 3000 ppm or less. Water remaining in the ionic compound is electrolyzed, and generated hydrogen ions are bonded with the above-mentioned halide ions to form hydrogen halides. In addition, in an electrolyte solution, hydrogen ions and halide ions exist while being dissociated, so that pH of the electrolyte solution is lowered (acidic). As a result, due to the produced acidic components in the electrolyte solution, the electrode material is dissolved and the capability of an electrochemical device is lowered. Consequently, the amount of water contained in the ionic compound is better as it is lower and it is preferably 1000 ppm or less and more preferably 500 ppm or less.

The ionic compound of the invention defined by the above-mentioned general formula (I) has low contents of impure ions attributed to the starting materials and impurities which are inevitably mixed in the synthesis process. Consequently, if the ionic compound of the invention is used as an ion conductor of various kinds of electrochemical devices, electrochemical devices with high reliability and which hardly cause decrease of ion conductivity and corrosion of peripheral members can be obtained.

Additionally, any of conventionally known measurement methods can be employed for measuring the contents of the above-mentioned impurities such as Si, halide ions and water; however examples of a measurement method includes methods such as atomic absorption spectrometry, ICP emission spectrometry (high-frequency inductively-coupled plasma emission spectrometry) and ion chromatography as described in Examples.

As represented by the above-mentioned general formula (I), the ionic compound of the invention is a compound composed of an organic or inorganic cation [Kt]$^{m+}$ and tetracyanoborate anion [B(CN)$_4$]$^-$. The cation [Kt]$^{m+}$ may include organic cations [Kt$^b$]$^{m+}$ such as onium cation, and also inorganic cations [Kt$^a$]$^{m+}$ such as Li$^+$, Na$^+$, Mg$^{2+}$, K$^+$, Ca$^{2+}$, Zn$^{2+}$, Ga$^{3+}$, Pd$^{2+}$, Sn$^{2+}$, Hg$^{2+}$, Rh$^{2+}$, Cu$^{2+}$ and Pb$^+$. Among them, those containing onium cations or Li cation as [Kt]$^{m+}$ are easy to be dissolved in an organic solvent and usable as a nonaqueous electrolyte solution and therefore preferable.

The above-mentioned onium cations are preferably those defined by the following general formula (II).

[Chemical Formula 3]

(II)

In the formula, L denotes C, Si, N, P, S, or O; each R may be same or different and denotes an organic group and respective R may be bonded with each other; s denotes a number of groups denoted by R bonded to L and satisfies s=(valence of L)+1–(number of double bonds directly bonded to L) and an integer of 2 to 4. The valence of L means 2 in the case L is S or O; 3 in the case L is N or P; and 4 in the case L is C or Si.

The above-mentioned "organic group" denoted by R means a hydrogen atom, fluorine atom or a group containing at least one carbon atom. The above-mentioned "a group containing at least one carbon atom" may be any group as long as the group contains at least one carbon atom and may have other atoms such as a halogen atom and a hetero-atom and also a substituent group. Examples of the substituent group may include an amino group, imino group, amido group, a group having an ether bond, a group having a thio-ether bond, an ester group, hydroxyl group, an alkoxy group, carboxyl group, carbamoyl group, cyano group, disulfide group, nitro group, nitroso group, sulfonyl group, etc.

Examples of the onium cations defined by the above-mentioned general formula (II) may be those defined by the following general formulas:

[Chemical Formula 4]

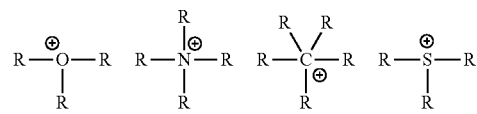

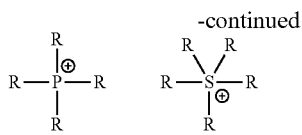

(wherein, each R denotes a same or different organic group and two or more of these may be bonded with each other) and preferably onium cations containing N, P, S or O for L, more preferably N for L. The onium cations may be used alone, or two or more may be used in combination. Preferable examples among them are onium cations defined by the following general formulas (III) to (VI).

Examples may be at least one kind cation among 14 types of heterocyclic onium cations defined by the following general formulas (III):

[Chemical Formula 5]

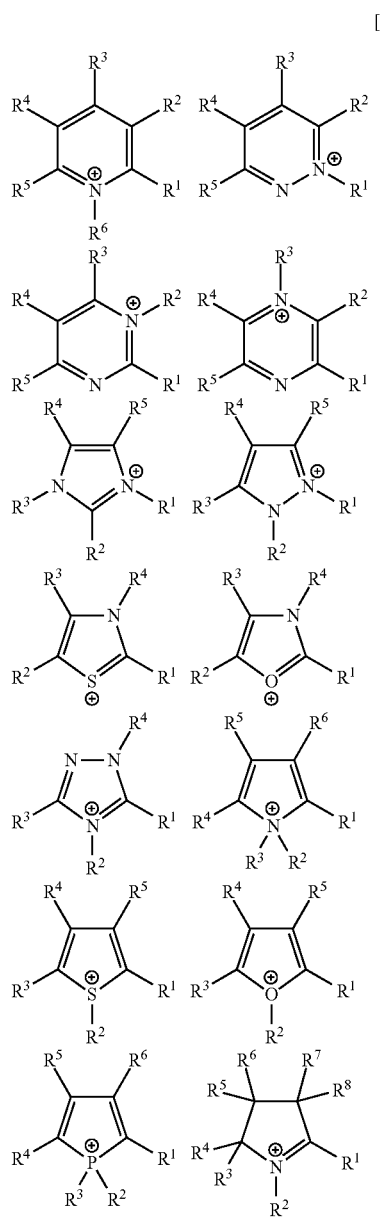

The organic groups denoted by $R^1$ to $R^8$ are same as those exemplified in the general formula (II). More particularly, $R^1$ to $R^8$ denote a hydrogen atom, a fluorine atom, or an organic group; and the organic group is preferably a straight or branched or cyclic hydrocarbon group (excluding a group which forms a ring by bonding groups denoted by $R^1$ to $R^8$) or a fluorocarbon group having 1 to 18 carbon atoms; more preferably a hydrocarbon group or a fluorocarbon group having 1 to 8 carbon atoms, and even more preferably a hydrocarbon group or a fluorocarbon group having 1 to 9 carbon atoms. Further, the organic group may contain a substituent group, a hetero atom such as nitrogen, oxygen or sulfur atom, or a halogen atom as exemplified in the above-mentioned general formula (II).

Examples may be at least one kind cation among 9 types of saturated cyclic onium cations defined by the following general formulas (IV):

[Chemical Formula 6]

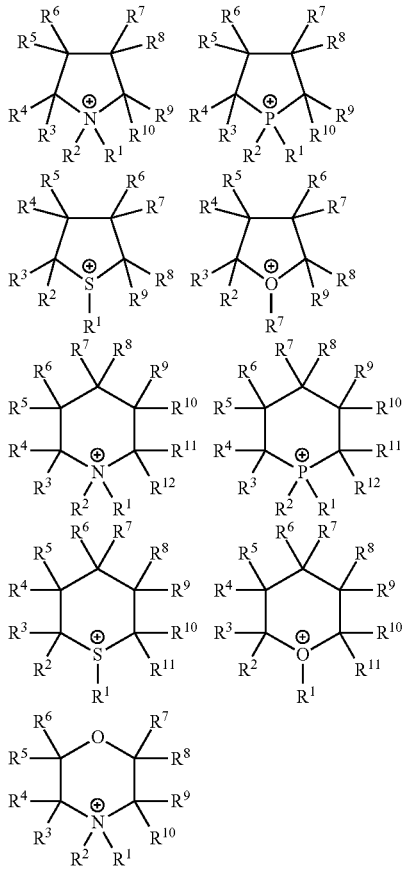

In the above-mentioned general formula, the organic groups denoted by $R^1$ to $R^{12}$ are same or different and may be bonded with one another.

Examples may be a aliphatic onium cation defined by the following general formulas (V) in which the groups denoted by $R^1$ to $R^4$ are same or different organic groups;

[Chemical Formula 7]

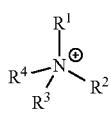

Examples of the above-mentioned aliphatic onium cations (V) may be quaternary ammoniums such as tetramethylammonium, tetraethylammonium, tetrapropylammonium, tetrabutylammonium, tetraheptylammonium, tetrahexylammonium, tetraoctylammonium, triethylmethylammonium, methoxyethyldiethylmethylammonium, trimethylphenylammonium, benzyltrimethylammonium, benzyltributylammonium, benzyltriethylammonium, dimethyldistearylammonium, diallyldimethylammonium, 2-methoxyethoxymethyltrimethylammonium, and tetrakis(pentafluoroethyl)ammonium; tertiary ammoniums such as trimethylammonium, triethylammonium, diethylmethylammonium, dimethylethylammonium, and dibutylmethylammonium; secondary ammoniums such as dimethylammonium, diethylammonium, and dibutylammonium; primary ammoniums such as methylammonium, ethylammonium, butylammonium, hexylammonium, and octylammonium; and ammonium compounds such as N-methoxytrimethylammonium, N-ethoxytrimethylammonium, N-propoxytrimethylammonium, and $NH_4$.

Among the onium cations of the above-mentioned (III) to (V), nitrogen atom-containing onium cations are preferable; quaternary ammoniums and imidazoliums are more preferable; and at least one kind among 5 kinds of onium cations defined by the following general formulas:

[Chemical Formula 8]

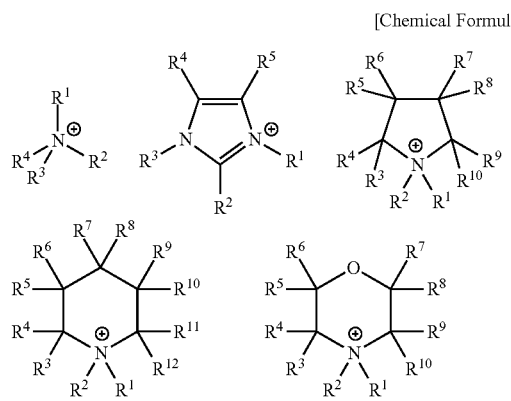

(wherein $R^1$ to $R^{12}$ are same as defined above) is particularly preferable.

Particularly preferable examples among the above exemplified ammoniums are alkyl quaternary ammoniums such as tetraethylammonium, tetrabutylammonium, and triethylmethylammonium; alkyl tertiary ammonium such as triethylammonium, dibutylmethylammonium, and dimethylethylammonium; imidazoliums such as 1-ethyl-3-methylimidazolium and 1,2,3-trimethylimidazolium; and pyrrolidiniums such as N,N-dimethylpyrrolidinium and N-ethyl-N-methylpyrrolidinium since they are easily made available.

The ionic compound of the invention has excellent physical properties such as heat resistance, electric conductivity, and withstand voltage. In addition, these physical values differ more or less depending on the type of the cation $Kt^{m+}$ composing the ionic compound; however the ionic compound of the invention indicates withstand voltage of +2.0 V or higher by measurement of potential window described later.
<Method for Producing Ionic Compound>

Next, a method for producing an ionic compound of the invention will be described.

The method for producing an ionic compound of the invention is characterized in that the ionic compound defined by the above-mentioned general formula (I) is produced by reaction of starting materials including a cyanide and a boron compound.

That is, the method for producing an ionic compound of the invention includes a first production method for obtaining the ionic compound defined by the above-mentioned general formula (I) by reaction of a specified cyanide $M^a(CN)_n$ and a boron compound; a second production method involving reaction of an ammonium cyanide type compound and a boron compound; a third production method involving reaction of trimethylsilyl cyanide (TMSCN), an amine and/or ammonium salt, and a boron compound; and a fourth production method involving reaction of hydrogen cyanide (HCN), an amine, and a boron compound. According to these production methods of the invention, an ionic compound containing tetracyanoborate can be obtained in a milder condition, or more efficiently, or less expensively than conventional methods. Hereinafter, these production methods will be described sequentially.

[First Production Method]

The method for producing an ionic compound of the invention is a method for producing an ionic compound containing tetracyanoborate ion and defined by the following general formula (I) and is characterized in that the method involves reaction of starting materials containing $M^a(CN)_n$ ($M^a$ denotes $Zn^{2+}$, $Ga^{3+}$, $Pd^{2+}$, $Sn^{2+}$, $Hg^{2+}$, $Rh^{2+}$, $Cu^{2+}$, or $Pb^+$; and n is an integer of 1 to 3), and a boron compound.

[Chemical Formula 9]

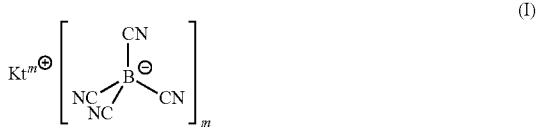

(wherein, $[Kt]^{m+}$ denotes an organic cation $[Kt^b]^{m+}$ or an inorganic cation $[Kt^a]^{m+}$; and m denotes an integer of 1 to 3).

To obtain the ionic compound containing tetracyanoborate ion, the inventors of the invention have found that use of a cyanide compound $M^a(CN)_n$ containing specified metal ion (any one of $Zn^{2+}$, $Ga^{3+}$, $Pd^{2+}$, $Sn^{2+}$, $Hg^{2+}$, $Rh^{2+}$, $Cu^{2+}$, and $Pb^+$) in place of an alkali metal cyanide such as potassium cyanide (KCN), which has been used conventionally as a starting material, makes it possible to stably obtain a compound defined by the above-mentioned general formula (I) in mild reaction condition.

As the cyanide compound $M^a(CN)_n$ of the invention, a cyanide compound of metal cation which is classified in metal cation with low energy levels between HOMO-2nd HOMO, that is, soft metal cations based on the HSAB rule, may be employed. It is because use of a cyanide compound with the above specified metal cation promotes the reaction quickly as compared with the case of using an alkali metal cyanide compound. The reason for that the above-mentioned metal cation is preferable is not made clear; however the inventors of the invention suppose as follows.

In general, based on the HSAB rule, alkali metal ions are classified in hard cations, and the specified metal contained in the cyanide compound on the invention is classified in soft cations. On the other hand, the tetracyanoborate anion (TCB), which is a product, is classified in soft anions. It is therefore supposed that since a combination of a soft acid and a soft base tends to form a stable ionic compound, the reaction of the cyanide compound in the invention tends to be promoted easily rather than that using a conventionally employed alkali metal cyanide of a hard cation such as Li⁺, Na⁺, and K⁺. Further, use of cyanides of these metals of the invention as starting materials makes it possible to obtain B(CN)$_4$ compound with few content of impurities at a high yield.

<Cyanide>

Among the above-mentioned cyanide M$^a$(CN)$_n$, preferable examples include at least one selected from a group consisting of Zn(CN)$_2$, Ga(CN)$_3$, Pd(CN)$_2$, Sn(CN)$_2$, Hg(CN)$_2$, and Cu(CN)$_2$.

<Boron Compound>

The above-mentioned boron compound is not particularly limited as long as it contains boron. Preferable to be used is at least one selected from a group consisting of, for example, M$^c$BX$^c_4$ (M$^c$ denotes a hydrogen atom or an alkali metal atom; X$^c$ denotes a hydrogen atom, a hydroxyl group, or a halogen atom; hereinafter the same); BX$^c_3$, BX$^c_3$-complex, B(OR$^{13}$)$_3$ (R$^{13}$ denotes a hydrogen atom or an alkyl group; hereinafter the same), B(OR$^{13}$)$_3$-complex, Na$_2$B$_4$O$_7$, ZnO B$_2$O$_3$, and NaBO$_3$.

Examples of M$^c$BX$^c_4$ are HBF$_4$, KBF$_4$, KBBr$_4$, NaB(OH)$_4$, KB(OH)$_4$, LiB(OH)$_4$, LiBF$_4$, NaBH$_4$, etc.; examples of BX % are BH$_3$, B(OH)$_3$, BF$_3$, BCl$_3$, BBr$_3$, BI$_3$, etc.; examples of BX$^c_3$-complex are complexes of the above-mentioned BX$^c_3$ with ethers such as diethyl ether, tripropyl ether, tributyl ether, and tetrahydrofuran and amines such as ammonia, methylamine, ethylamine, butylamine, hexylamine, octylamine, dimethylamine, diethylamine, dibutylamine, dihexylamine, dicyclohexylamine, trimethylamine, triethylamine, tributylamine, triphenylamine, guanidine, aniline, morpholine, pyrrolidine and methylpyrrolidine; examples of B(OR$^{13}$)$_3$ are boric acid, boron compounds having an alkoxy group of 1 to 10 carbon atoms, etc. Preferable compounds among these compounds are NaBH$_4$, BH$_3$, BF$_3$, BCl$_3$, BBr$_3$, B(OMe)$_3$, B(OEt)$_3$, Na$_2$B$_4$O$_7$, and B(OH)$_3$ which have relatively high reactivity; more preferable compounds are BF$_3$, BCl$_3$, BBr$_3$, etc., BX$^c_3$ in which X$^c$ is a halogen atom, and B(OR$^{13}$)$_3$ having an alkoxy group of 1 to 4 carbon atoms such as B(OMe)$_3$ and B(OEt)$_3$; and even more preferable compounds are BCl$_3$, B(OMe)$_3$, and B(OEt)$_3$. The above-mentioned boron compounds may be used alone and two or more of them may be used in combination. In terms of decrease of the impurity amount derived from F, use of a compound containing no F atom among these boron compounds is recommended.

In the first production method, at the time of reacting the above-mentioned cyanide M$^a$(CN)$_n$ with a boron compound, furthermore it is preferable to use an ionic substance defined by the general formula: KtX$^b$ ([Kt]$^{m+}$ is a cation with m valence; [X$^b$]$^{m-}$ is an anion with m valence; and m is an integer of 1 to 3; and hereinafter, the same) as a starting material.

Examples of the cation [Kt]$^{m+}$ composing the above-mentioned ionic substance KtX$^b$ include organic cations [Kt$^b$]$^{m+}$ such as onium cations and inorganic cations [Kt$^a$]$^{m+}$ such as Li⁺, Na⁺, Ca²⁺, K⁺, Zn²⁺, Ga³⁺, Pd²⁺, Sn²⁺, Hg²⁺, Rh²⁺, Cu²⁺, and Pb⁺. Among these, onium cations defined by the above-mentioned general formulas (III) to (V) are particularly preferable as [Kt$^b$]$^{m+}$ composing the ionic substance in the invention. When an ionic substance Kt$^b$X$^b$ having an onium cation as [Kt]$^{m+}$ is used for the starting material, it brings advantageous consequence that an onium salt of [B(CN)$_4$]⁻ which is an desired product can be obtained by one step reaction and also cyanidation reaction is easily caused owing to mutual action between M$^a$(CN)$_n$ and the ionic substance Kt$^b$X$^b$.

The mixing ratio of the above-mentioned starting materials is adjusted to be preferably 1:1 to 100:1 (cyanide M$^a$(CN)$_n$: boron compound, mol ratio). It is more preferably 1:1 to 50:1; furthermore preferably 1:1 to 20:1; and even more preferably 1:1 to 10:1. If the mixing amount of the cyanide M$^a$(CN)$_n$ is too low, the production amount of the aimed ionic compound may possibly be low or byproducts (e.g. tricyanoborate, dicyanoborate, etc.) may be produced. On the other hand, if the mixing amount of the cyanide M$^a$(CN)$_n$ is too high, the amount of impurities derived from CN is increased and it tends to be difficult to refine the desired product.

In the case the ionic substance KtX$^b$ is contained in the above-mentioned starting materials, the mixing ratio of the ionic substance to the boron compound is preferably to be 100:1 to 1:100 (ionic substance: boron compound, mol ratio). It is more preferably 50:1 to 1:50 and furthermore preferably 20:1 to 1:20. In the case the mixing amount of the ionic substance is too low, the production amount of the aimed ionic compound may possibly be low and on the other hand, if the mixing amount of the ionic substance is too high, the amount of impurities derived from the ionic substance is increased and it sometimes tends to be difficult to refine the desired product.

To evenly promote the reaction in the method for producing an ionic compound of the invention, it is preferable to use a reaction solvent. The reaction solvent is not particularly limited as long as it can dissolve the above-mentioned starting materials, and water or an organic solvent may be used as the reaction solvent. Examples of the organic solvent include hydrocarbon such as toluene, xylene, benzene, and hexane; chloride such as chloroform and dichloromethane; ether such as diethyl ether, cyclohexyl methyl ether, dibutyl ether, dimethoxyethane, and dioxane; ester such as ethyl acetate and butyl acetate; ketone such as 2-butanone and methyl isobutyl ketone; alcohol such as methanol, ethanol, 2-propanol, and butanol; acetonitrile, tetrahydrofuran, γ-butyrolactone, dimethyl sulfoxide, dimethylformamide, etc. The above-mentioned reaction solvents may be used alone or two or more of them may be used in form of a mixture.

The condition at the time of reacting the starting materials is not particularly limited and may be properly adjusted in accordance with the advancing state of the reaction; however, for example, the reaction temperature is adjusted to be preferably 0° C. to 200° C. It is more preferably 20° C. to 150° C. and even more preferably 50° C. to 130° C. The reaction time is adjusted to be preferably 0.2 hours to 200 hours, more preferably 0.5 hours to 150 hours, and even more preferably 1 hour to 100 hours.

In the first production method, in the case the above-mentioned metal cyanide and boron compound are used as the starting materials, an ionic compound defined by the general formula: Kt$^a$[B(CN)$_4$]$_m$ ([Kt$^a$]$^{m+}$ is the metal cation [M$^a$]$^{n+}$ of the cyanide) is produced. Further, as described above, in the case the starting materials include the ionic substance KtX$^b$ ([Kt]$^{m+}$ is the onium cation [Kt$^b$]$^{m+}$ or the inorganic cation [Kt$^a$]$^{m+}$) or the produced ionic compound Kt$^a$[B(CN)$_4$]$_m$ ([Kt$^a$]$^{m+}$ is the metal cation [M$^a$]$^{n+}$ of the cyanide) is cation-exchanged by reaction with the ionic substance KtX$^b$, an ionic compound Kt[B(CN)$_4$]$_m$ having a desired onium cation or inorganic cation can be obtained. The above-mentioned cation exchange reaction with the ionic substance will be described later.

Accordingly, the first production method of the invention includes three embodiments: an embodiment of producing the ionic compound Kt$^a$[B(CN)$_4$]$_m$ of the invention ([Kt$^a$]$^{m+}$ the metal cation [M$^a$]$^{n+}$ of the cyanide) by reaction of the above-mentioned cyanide M$^a$(CN)$_n$ and boron compound; an embodiment of producing the ionic compound Kt[B(CN)$_4$]$_m$ of the invention ([Kt]$^{m+}$ is onium cation [Kt$^b$]$^{m+}$ or the inorganic cation [Kt$^b$]$^{m+}$) by obtaining Kt$^a$[B(CN)$_4$]$_m$ by reaction of the above-mentioned metal cyanide $M^a(CN)_n$ and a boron compound and thereafter cation-exchange reaction of the obtained compound with an ionic substance $KtX^b$: and an embodiment of producing the ionic compound $Kt[B(CN)_4]_m$ of the invention ($[Kt]^{m+}$ is onium cation $[Kt^b]^{m+}$ or the inorganic cation $[Kt^a]^{m+}$) by one-step reaction of the above-mentioned metal cyanide $M^a(CN)_n$, a boron compound, and an ionic substance $KtX^b$. Accordingly, the ionic compound $Kt^{m+}[\{B(CN)_4\}^-]_m$ of the invention obtained by the first production method includes both cases, that is, $[Kt]^{m+}$ is an onium cation $[Kt^b]^{m+}$ and $[Kt]^{m+}$ is an inorganic cation $[Kt^a]^{m+}$.

According to the first production method of the invention using the above-mentioned cyanide $M^a(CN)_n$ as a CN reagent, an ionic compound having tetracyanoborate ion ($[B(CN)_4]^-$) can be obtained even in a reaction condition in which it is impossible to stably obtain an aimed compound by using an alkali metal cyanide (KCN).

[Second Production Method]

Next, the second production method will be described. The second method for producing an ionic compound of the invention is characterized in that an ionic compound defined by the following general formula (I) is obtained by reaction of an ammonium cyanide type compound defined by the following general formula (VI) and a boron compound.

[Chemical Formula 10]

(VI)

(wherein, the bond between N—R is a saturated bond and/or an unsaturated bond; t denotes the number of groups R bonded to N, satisfies t=4−(number of double bonds bonded to N), and is an integer of 3 to 4; respective R independently denote a hydrogen atom or an organic group and two or more of them may be bonded).

[Chemical Formula 11]

(I)

(wherein, $[Kt]^{m+}$ denotes an organic cation $[Kt^b]^{m+}$ or an inorganic cation $[Kt^a]^{m+}$; and m denotes an integer of 1 to 3).

In order to synthesize the ionic compound containing tetracyanoborate ion, the inventors have found that use of an ammonium cyanide type compound in place of an alkali metal cyanide such as potassium cyanide which has been used conventionally as a cyanide (CN) source makes it possible to obtain an ionic compound defined by the above-mentioned general formula (I) efficiently at a lower reaction temperature.

The inventors of the invention suppose the reason for that the reaction is promoted in the milder condition than that in a conventional method by using the ammonium cyanide type compound as a cyanide source and the product is obtained more efficiently is as follows. With respect to an alkali metal cyanide, the bond between the alkali metal ion and cyano group (CN) is strong. On the other hand, with respect to an ammonium type cyanide, since the N atom bearing positive charge has steric hindrance, the cyanide ion is hard to approach to the N atom and thus the bond between CN and N atom is relatively weak. In this connection, in the reaction of producing a tetracyanoborate, it is supposed that if free cyanide ion in the reaction system is generated, the bond with the boron compound tends to be formed easily and as a result, the desired TCB is efficiently produced. Consequently, in the production method of the invention using the ammonium type cyanide having a weak N—CN bond, it is supposed that the cyanide ion can be released quickly even in mild reaction condition and reaction is promoted to produce TCB.

Consequently, the organic cation $[Kt]^{m+}$ composing the ionic compound $Kt[B(CN)_4]_m$ obtained by the second production method of the invention includes those derived from the cations contained in ammonium cyanide type compounds; those derived from cations contained in boron compounds; and also those derived from cations contained in ionic substances to be employed for cation exchange reaction described later.

<Ammonium Cyanide Type Compound>

At first, an ammonium cyanide type compound defined by the above-mentioned general formula (VI) will be described.

In the second production method, an ammonium cyanide type compound $[N-(R)_t]CN$ is used as a starting material. Use of the ammonium cyanide type compound, as a CN source for TCB synthesis reaction, makes it possible to obtain an ionic compound containing tetracyanoborate $[B(CN)_4]^-$ even in reaction condition in which the desired compound cannot be obtained in the case an alkali metal cyanide is used as a starting material.

In the ammonium $[N^{+-}(R)_t]$ composing the ammonium cyanide type compound defined by the above-mentioned general formula (VI), the N—R bond is a saturated bond and/or an unsaturated bond; t denotes the number of groups R bonded to N, satisfies t=4−(number of double bonds bonded to N), and is an integer of 3 to 4; respective R independently denote a hydrogen atom or an organic group and two or more of them may be bonded.

Additionally, the above-mentioned "organic group" may be same as those exemplified in the above-mentioned general formula (II).

Further, R may be bonded with N, which is the center element of ammonium, through a carbon atom composing the main structure of the organic group R and also may be bonded with N through another atom other than carbon or the above-mentioned substituent group. Moreover, in the case two or more organic groups R are bonded, the bonds may be a bond between a carbon atom composing the main structure of the organic groups R and other atom, also a bond between the carbon atom and a substituent group contained in the organic group R, and further a bond between substituent groups which are contained in two or more organic groups R respectively.

Preferable examples of the ammonium $[N^+-(R)_t]$ having the above-mentioned organic group R are those having the structure defined by the following general formula (VII) to (IX).

(VII) That is, nine kinds of ammonium-type derivatives defined by the following general formula in which t=3 and two R among three R form a ring structure;

[Chemical Formula 12]

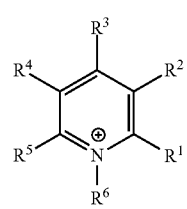

(VII-1)

Pyridinium derivative

Pyridazinium derivative (VII-2)

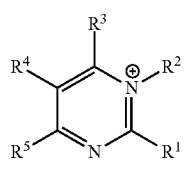

Pyrimidinium derivative (VII-3)

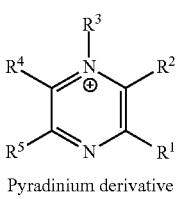

Pyradinium derivative (VII-4)

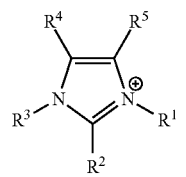

Iimidazolium derivative (VII-5)

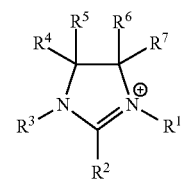

Imidazolinium derivative (VII-6)

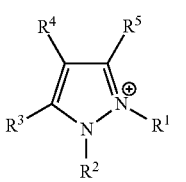

Pyrazolium derivative (VII-7)

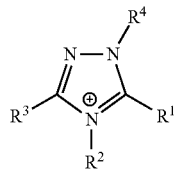

Triazolinium derivative (VII-8)

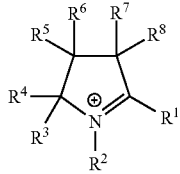

Pyrrolinium derivative (VII-9)

(VIII) Four kinds of ammonium-type derivatives defined by the following general formula in which t=4 and two R among four R form a ring structure;

[Chemical Formula 13]

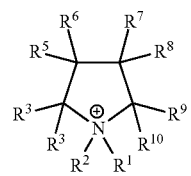

Pyrrolidinium derivative (VIII-1)

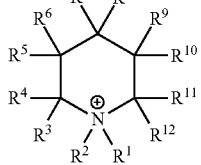

Piperidinium derivative (VIII-2)

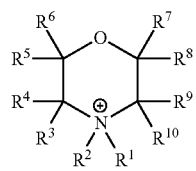

Morpholinium derivative (VIII-3)

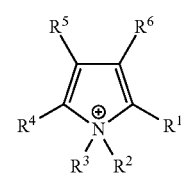

Pyrrolidinium derivative (VIII-4)

In the above-mentioned derivatives represented by the general formulas (VII) to (VIII), $R^1$ to $R^{12}$ independently denote a hydrogen atom or an organic group and two or more R may be bonded; and (IX) Alkylammonium derivatives defined by the following general formula in which t=4 and four R are not bonded to one another;

[Chemical Formula 14]

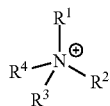

(IX)

Alkylammonium derivative

R$^1$ to R$^4$ composing the above-mentioned alkylammonium derivatives independently denote a hydrogen atom or an organic group.

Examples of the alkylammonium derivatives defined as (IV) include ammoniums and ammonium compounds exemplified as the above-mentioned aliphatic onium cations (V).

Preferable examples among the ammoniums defined as (VII) to (IX) are those having the structure defined by the following six types of general formulas.

[Chemical Formula 15]

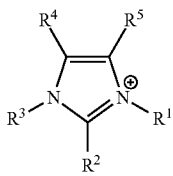

(VII-5)

Iimidazolium derivative

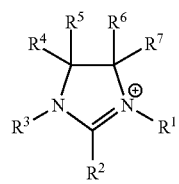

(VII-6)

Imidazolinium derivative

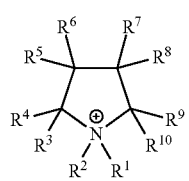

(VIII-1)

Pyrrolidinium derivative

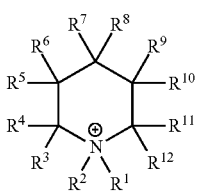

(VIII-2)

Piperidinium derivative

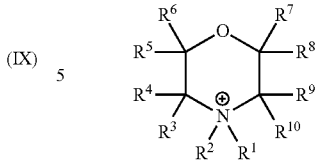

(VIII-3)

Morpholinium derivative

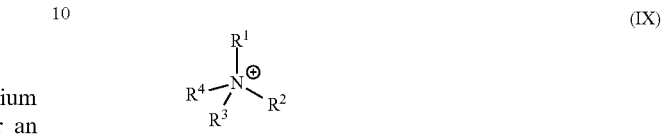

(IX)

Alkylammonium derivative (wherein, R$^1$ to R$^{12}$ denote as described above).

In the above-mentioned general formulas, R$^1$ to R$^{12}$ denote a hydrogen atom, a fluorine atom, or an organic group; and examples of the organic group are same as those exemplified for the above-mentioned general formula (III).

Particularly preferable examples among the above-exemplified ammonium-containing ammonium cyanides, salts of alkyl quaternary ammoniums and cyanide ion such as tetrabutylammonium cyanide, tetraethylammonium cyanide, and triethylmethylammonium cyanide; salts of alkyl tertiary ammonium and cyanide ion such as triethylammonium cyanide, dibutylmethylammonium cyanide, and dimethylethylammonium cyanide; salts of imidazolium and cyanide ion such as 1-ethyl-3-ethylimidazolium cyanide and 1,2,3-trimethylimidazolium cyanide; and salts of pyrrolidinium and cyanide ion such as N,N-dimethylpyrrolidinium cyanide and N-ethyl-N-methylpyrrolidinium cyanide, since these salts are easily made available.

The ammonium cyanide may be an ammonium cyanide containing a single ammonium, or the ammonium cyanide containing two or more different kinds of ammonium may be used in form of a mixture.

The ammonium cyanide can be synthesized by reaction of a compound defined by the following general formula (X) and a metal cyanide L$^{p+}$[(CN)$^-$]$_n$ (L$^{p+}$ denotes a metal cation; p is 1 to 4 or preferably 1 or 2).

[Chemical Formula 16]

(X)

(wherein [N—(R)$_t$] denotes same as defined by the general formula (VI); Y denotes a halide ion, BF$_4^-$, PF$_6^-$, SO$_4^{2-}$, HSO$_4^-$, ClO$_4^-$, NO$_3^-$, or R$^{13}$O$^-$ (R$^{13}$ denotes a hydrogen atom or an organic group); l denotes 1 or 2; and additionally, R$^{13}$ is same as R$^1$ to R$^{12}$).

In the above-mentioned general formula (X), [N$^+$—(R)$_t$] corresponds with the ammonium cation of the above-mentioned ammonium cyanide, and concrete examples of [N$^+$—(R)$_t$] include tetrabutylammonium, triethylmethylammonium, tetraethylammonium, triethylammonium, dibutylammonium, dimethylammonium, 1-ethyl-3-methylimidazolium, N,N-dimethylpyrrolidinium, N,N-methylbutylpyrrolidinium, ammonium (NH$_4^+$), morpholium, etc. Concretely, preferable examples of the compounds (X) include tetrabutylammonium sulfoxide, tetraethylammonium chloride, triethylammonium chloride, 1-ethyl-3-methylimidazolium bromide, etc.

In the above-mentioned metal cyanide L$^{p+}$[(CN)$^-$]$_n$, L$^{p+}$ denotes an alkali metal ion, an alkaline earth metal ion, Zn$^{2+}$, Cu$^+$, Cu$^{2+}$, Pd$^{2+}$, Au$^+$, Ag$^{2+}$, Al$^{3+}$, Ti$^{4+}$, Fe$^{3+}$, Ga$^{3+}$, etc., and more preferably an alkali metal ion, an alkaline earth metal ion, $Zn^{2+}$, $Cu^+$, $Cu^{2+}$, and $Ag^{2+}$. Concrete examples of the metal cyanide include KCN, LiCN, NaCN, $Mg(CN)_2$, $Ca(CN)_2$, $Zn(CN)_2$, CuCN, $Cu(CN)_2$, etc.

The mixing ratio of the above-mentioned compound (X) and the metal cyanide is adjusted to be preferably 40:1 to 1:40 (compound (X):metal cyanide, mol ratio), more preferably 20:1 to 1:20, and even more preferably 10:1 to 1:10.

The condition at the time of the above-mentioned reaction is not particularly limited and for example, the reaction temperature is adjusted to be preferably 0° C. to 150° C. and more preferably 20° C. to 100° C. and reaction time is adjusted to be preferably 0.01 hours to 20 hours and more preferably 0.05 hours to 5 hours. Further, a reaction solvent may be used or may not be used; preferable examples of the reaction solvent are diethyl ether, dibutyl ether, tetrahydrofuran, dioxane, dichloromethane, chloroform, carbon tetrachloride, ethyl acetate, butyl acetate, acetone, 2-butanone, methyl isobutyl ketone, acetonitrile, benzonitrile, dimethoxyethane, and water. These reaction solvents may be used alone or two or more of them may be used in combination. Additionally, use of two or more kinds of the reaction solvents is one of preferable conditions of the above-mentioned reaction.

<Boron Compound>

In the second production method of the invention, the ionic compound defined by the above-mentioned general formula (I) is synthesized by reaction of starting materials containing the above-mentioned ammonium cyanide and boron compound. As the boron compound, it is not particularly limited as long as the compound contains boron and those same as exemplified in the first production method can be employed.

The mixing ratio of the above-mentioned starting materials is adjusted to be preferably 50:1 to 4:1 (ammonium cyanide: boron compound, mol ratio). It is more preferably 20:1 to 4:1 and even more preferably 10:1 to 4:1. If the mixing amount of the ammonium cyanide is too low, the production amount of the desired ionic compound may possibly be low or byproducts (e.g. tricyanoborate, dicyanoborate, etc.) may be produced in some cases. On the other hand, if the mixing amount of the ammonium cyanide is too high, the amount of impurities derived from CN is increased and it tends to be difficult to refine the desired product.

In the method for producing an ionic compound of the invention, to evenly promote the reaction, it is preferable to use a reaction solvent. The reaction solvent is not particularly limited as long as it can dissolve the above-mentioned starting materials, and water or an organic solvent may be used as the reaction solvent. The organic solvent may be same as those exemplified in the first production method. Particularly, preferable solvents are hydrocarbon, ether, and ester. The above-mentioned reaction solvents may be used alone or two or more of them may be used in form of a mixture.

The condition at the time of reacting the starting materials is not particularly limited and may be properly adjusted in accordance with the advancing state of the reaction; for example, the reaction temperature is adjusted to be preferably 30° C. to 200° C. It is more preferably 50° C. to 170° C. and even more preferably 80° C. to 150° C. The reaction time is adjusted to be preferably 0.2 hours to 200 hours, more preferably 0.5 hours to 150 hours, and even more preferably 1 hour to 100 hours.

According to the second production method of the invention in which the above-mentioned ammonium cyanide is used as a CN source, an ionic compound having tetracyanoborate ion ($[B(CN)_4]^-$) is obtained even in reaction condition of 200° C. or lower at which the desired product cannot be obtained if an alkali metal cyanide is used.

[Third Production Method]

The third method for producing an ionic compound of the invention is characterized in that an ionic compound defined by the following general formula (I) is obtained by reaction of trimethylsilyl cyanide (TMSCN), an amine and\or an ammonium salt, and a boron compound.

[Chemical Formula 17]

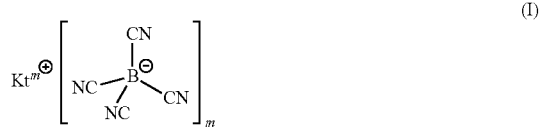

(I)

(wherein, $[Kt]^{m+}$ denotes an organic cation $[Kt^b]^{m+}$ or an inorganic cation $[Kt^a]^{m+}$; and m denotes an integer of 1 to 3).

In synthesis of the ionic compound having tetracyanoborate ion, the inventors of the invention have found that the ionic compound defined by the above-mentioned general formula (I) can be obtained at a high efficiency by using trimethylsilyl cyanide as a cyanide (CN) source in place of an alkali metal cyanide such as potassium cyanide, which is used conventionally, and carrying out reaction with a boron compound in presence of an amine and/or ammonium salt.

The inventors of the invention suppose the reason for that the product is obtained by reaction of trimethylsilyl cyanide and a boron compound under the presence of an amine and/or ammonium salt at a higher yield than that by a conventional method is as follows.

In the reaction for producing the tetracyanoborate, it is assumed that a compound, which generates free cyanide ion in the reaction system, is easy to form a bond with the boron compound and easy to produce the desired TCB. Therefore, the inventors investigate the bonding state between cyanide ion and alkali metal ion or trimethylsilane. An alkali metal cyanide has no bulky substituent group which hind the bond between the alkali metal ion and cyano group (CN). Thus it is supposed that a strong bond is formed. On the other hand, in trimethylsilyl cyanide, methyl groups are bonded to cationic Si atom and the methyl groups create steric hindrance, so that cyanide ion is hard to approach to the Si atom, and thus the bond between CN and Si atom is supposed to be relatively weak. Consequently, in the production method of the invention using trimethylsilyl cyanide having a weak Si—CN bond, it is supposed that the cyanide ion is released quickly and reacted to give TCB.

The ionic compound composed of trimethylsilyl cation and TCB is extremely instable and easy to be decomposed. However, in the invention, it is supposed that since trimethylsilyl cation is quickly replaced with ammonium cation, the TCB-containing ionic compound is obtained stably. Further, although a detailed reason is unclear, in the case of using an amine, it is supposed that the amine catches protons generated from the starting materials and intermediate products, and produces an ammonium compound by the reaction. As a result, it is assumed that a stable TCB-containing ionic compound is obtained in the same manner as that in the case of using an ammonium salt. Because of these reasons, it is supposed that the TCB production reaction is quickly promoted to produce the ionic compound by carrying out the above-mentioned reaction in presence of an amine and/or ammonium salt. In addition, in the production method of the invention, since the reaction is carried out in presence of an amine and/or ammonium salt, there is an advantage that an ionic compound having ammonium as a cation is obtained in one step.

<Trimethylsilyl Cyanide>

At first, trimethylsilyl cyanide as a starting material will be described.

In the third production method, trimethylsilyl cyanide is used as a starting material. Use of trimethylsilyl cyanide as a CN source for TCB synthesis reaction makes it possible to obtain the ionic compound having tetracyanoborate $[B(CN)_4]^-$ even in a reaction condition in which it is difficult to obtain a desired compound in a case of using an alkali metal cyanide as a starting material.

Trimethylsilyl cyanide to be used may be commercialized ones and also those synthesized by conventional method. A method for synthesizing TMSCN is not particularly limited; however, for example, a method using starting materials containing a compound having a trimethylsilyl group (TMS group) and hydrogen cyanide (HCN) is preferable, since the method can synthesizes TMSCN more economically.

Examples of the compound containing a TMS group may be $TMSX^1$ ($X^1$ is OR, a halogen atom, or hydroxyl group), hexamethyldisilazane (TMS—NH-TMS), etc. Concretely, a method for reacting $TMSX^1$ ($X^1$ is a halogen atom) with hydrogen cyanide in presence of an amine such as triethylamine (reference to the following reaction formula (XI-1); Stec, W. J., et al., Synthesis. 1978:154.) and a method for reacting hexamethyldisilazane with hydrogen cyanide (reference to the following reaction formula (XI-2)) can be employed.

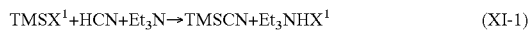  (XI-1)

  (XI-2)

Further, since the above-mentioned hexamethyldisilazane can work as an amine, hexamethyldisilazane and a compound having trimethylsilyl group may be used simultaneously (reference to the following reaction formula (XI-3)). Consequently, ammonia produced as a byproduct is trapped in the system and a problem of odor can be suppressed and therefore, it is preferable.

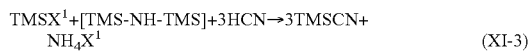  (XI-3)

The mixing ratio of the raw materials is adjusted to be preferably 20:1 to 1:20 (mol ratio), more preferably 10:1 to 1:10, and even more preferably 5:1 to 1:5 of trimethylsilyl group and hydrogen cyanide (HCN). That is, in the case hexamethyldisilazane is used, or hexamethyldisilazane and a trimethylsilyl group-containing compound are used in combination, the total amount of trimethylsilyl groups contained in the raw materials and the addition amount of hydrogen cyanide are controlled to be within the above-mentioned range. The reaction temperature is preferably −20° C. to 100° C. and more preferably 0° C. to 50° C., and the reaction time is preferably 0.5 hours to 100 hours and more preferably 1 hour to 50 hours.

Additionally, in the third production method, a trimethylsilyl group-containing compound is produced as a byproduct (e.g. $TMSX^1$, TMS-O-TMS, etc.; reference to the following expression).

  (XI-4)

($X^2$ and $X^3$ denote OR, a halogen atom, or hydroxyl group).

Therefore, in the third production method, TMSCN regenerated by reaction of the trimethylsilyl group-containing compound $TMSX^1$ produced as a byproduct with HCN may be utilized as a starting material. Because TMSCN is expensive and the production cost of the ionic compound can be suppressed by recycling of $TMSX^1$, which is a byproduct.

<Boron Compound>

In the third production method of the invention, the ionic compound defined by the above-mentioned general formula (I) is synthesized by reacting starting materials containing the above-mentioned TMSCN, amine and/or ammonium salt, and boron compound. The above-mentioned boron compound is not particularly limited as long as it is a boron-containing compound and those same as exemplified in the first production method can be used.

The mixing ratio of the above-mentioned starting materials is preferably 3:1 to 80:1 (TMSCN:boron compound, mol ratio). It is more preferably 4:1 to 40:1 and even more preferably 4:1 to 20:1. If the mixing amount of TMSCN is too low the production amount of the desired ionic compound may possibly be low or byproducts (e.g. tricyanoborate, dicyanoborate, etc.) may be produced in some cases. On the other hand, if the mixing amount of TMSCN is too high, the amount of impurities derived from CN is increased and it tends to be difficult to refine the desired product.

<Amine and/or Ammonium Salt>

In the invention, the above-mentioned reaction of TMSCN and the boron compound is carried out in presence of an amine and/or ammonium salt. The amine becomes an ammonium salt in the reaction system, and the produced ammonium salt is exchanged with trimethylsilyl cation of a TCB compound comprising trimethylsilyl as a cation, which is produced separately in the reaction system, to obtain a stable ionic compound containing TCB at a high yield. Further, since an amine and/or ammonium salt is used, an ionic compound containing ammonium as a cation component can be obtained in one step without carrying out cation exchange reaction.

Amines usable in the invention are preferably amines defined by the following general formula (XII).

[Chemical Formula 18]

  (XII)

In the general formula (XII), the bond between N—R is a saturated bond and/or unsaturated bond; u denotes the number of groups R bonded to N, satisfies u=3-(number of double bonds bonded to N), and is 2 or 3; respective R independently denote a hydrogen atom, a fluorine atom or an organic group and two or more R may be bonded to form a ring. Additionally, examples of the above-mentioned "organic group" may be same as those exemplified in the above-mentioned general formula (II).

Examples of the amine defined by the above-mentioned general formula (XII) include amine compounds (XIII) and (XIV) which have a saturated or unsaturated cyclic structure in which two or more R are bonded, and an amine compound (XV) in which R are aliphatic.

(XIII) Amine compounds having a saturated or unsaturated cyclic structure defined by the above-mentioned general formula (XII) in which u is 3 and two or more R are bonded;

[Chemical Formula 19]

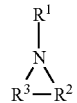  (XIII-1)

-continued

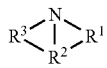
(XIII-2)

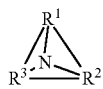
(XIII-3)

In the general formulas (XIII-1) to (XIII-3), $R^1$ to $R^3$ denote a hydrogen atom, a fluorine atom, or an organic group; and examples of the organic group are same as those exemplified for the above-mentioned general formula (III).

Concrete examples of compound defined by the above-mentioned general formulas (XIII-1) to (XIII-3) include compounds defined by the general formula (XIII-1) such as pyrrole, pyrrolidine, piperidine and morpholine; compounds defined by the general formula (XIII-2) such as 1,4-diazabicyclo[2.2.2]octane (DABCO); compounds defined by the general formula (XIII-3) such as hexamethylenetetramine; and derivatives of these compounds.

(XIV) Amine compounds having an unsaturated cyclic structure defined by the above-mentioned general formula (XII) in which u is 2 and two R are bonded.

[Chemical Formula 20]

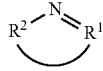
(XIV)

(in the general formula (XIV), $R^1$ and $R^2$ are same as those in the compound (XIII)).

Concrete examples of compound defined by the above-mentioned general formula (XIV) include compounds having amidine structure such as imidazole, imidazoline, pyrazole, triazole, pyrroline, diazabicyclononene (DBN) and diazabicycloundecene (DBU), and their derivatives; pyridine, pyridazine, pyrimidine, pyrazine, and their derivatives.

(XV) Amine compounds defined by the following general formulas and having a structure defined by the above-mentioned general formula (XII) in which u is 2 or 3 and no R is bonded.

[Chemical Formula 21]

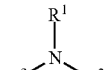
(XV-1)

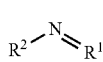
(XV-2)

(in the above-mentioned general formulas (XV), $R^1$ to $R^3$ are same as those in the compound (VIII)).

Examples of the amine compounds defined by the above-mentioned general formula (XV-1) in which u is 3 include trialkylamines such as trimethylamine, triethylamine, tributylamine, tripropylamine, diethylmethylamine, dibutylmethylamine, dihexylmethylamine, and dipropylamine; dialkylamines such as dimethylamine, diethylamine, dibutylamine, and dihexylamine; and monoalkylamines such as methylamine, ethylamine, butylamine, pentylamine, hexylamine, and octylamine. Examples of the compounds defined by the above-mentioned general formula (XV-2) in which n is 2 include guanidine and the like.

Preferable examples of amines defined by the above-mentioned general formulas (VIII) to (XV) are aliphatic amines such as triethylamine, tributylamine, butyldimethylamine, diethylamine, dibutylamine, butylamine, hexylamine, octylamine, and guanidine; cyclic amines such as piperidine, 1,4-diazabicyclo[2.2.2]octan (DABCO), imidazoline, diazabicyclononene (DBN), and diazabicycloundecene (DBU); and aromatic amines such as pyridine, imidazole, methylimidazole, and pyrazine. Among them, aliphatic amines such as triethylamine and dibutylamine have high basicity and are economical and therefore preferable.

On the other hand, as an ammonium salt, ammonium salts having ammonium cation defined by the above-mentioned general formulas (VII) to (IX) can be employed and particularly, salts having quaternary ammonium as a cation are preferable and concretely, one or more compounds selected from a group consisting of compounds defined by the following general formulas (XVII-1) to (XVII-5) are preferable.

[Chemical Formula 22]

(XVII-1)

(XVII-2)

(XVII-3)

(XVII-4)

(XVII-5)

In the formulas, respective R independently denote a hydrogen atom, a fluorine atom, or an organic group; and examples of the organic group defined by R in the above-mentioned general formulas are same as those exemplified for the above-mentioned general formula (II).

Concrete examples of an ammonium cation include ammonium, triethylmethylammonium, tetramethylammonium, tetraethylammonium, tetrabutylammonium, proton adduct of diazabicyclooctane, imidazolium, methylimidazolium, ethylmethylimidazolium, pyridinium, methylpyridinium, etc. and, especially preferable examples among them are triethylmethylammonium, tetramethylammonium, tetraethylammonium, tetrabutylammonium, proton adduct of diazabicyclooctane, and ethylmethylimidazolium; and even more preferable examples are triethylmethylammonium, tetramethylammonium, tetraethylammonium, and ethylmethylimidazolium.

Examples of an anion composing a salt with the above-mentioned ammonium cations include a halide ion, cyanide ion ($CN^-$), hydroxy ion ($OH^-$), cyanate ion ($OCN^-$), thiocyanate ion ($SCN^-$), an alkoxy ion ($RO^-$), sulfate ion, nitrate ion, acetate ion, carbonate ion, perchlorate ion, an alkylsulfate ion, an alkylcarbonate ion, etc. Especially, among these ions, a halide ion is preferable and $Cl^-$ or $Br^-$ is particularly preferable.

Examples of a preferable ammonium salt are those obtained by combining the above-mentioned ammonium cations and the above-mentioned anions and particularly preferable examples are tetrabutylammonium bromide, triethylmethylammonium chloride, tetraethylammonium chloride, ethylmethylimidazolium chloride, ammonium methoxide, pyridinium hydroxide, and tetraethylammonium cyanate.

The use amount of the above-mentioned amine and/or ammonium salt to the boron compound is adjusted to be preferably 0.1:1 to 10:1 (boron compound: amine and/or ammonium salt, mol ratio). It is more preferably 0.2:1 to 5:1 and even more preferably 0.5:1 to 2:1. If the mixing amount of the amine and/or ammonium salt is too low, removal of byproducts may become insufficient and the cation amount may be too deficient to produce the desired product efficiently in some cases. On the other hand, if the mixing amount of the amine and/or ammonium salt is too high, the amine and/or ammonium salt tends to remain as impurities.

To evenly promote the reaction in the method for producing an ionic compound of the invention, it is preferable to use a reaction solvent. The reaction solvent is not particularly limited as long as it can dissolve the above-mentioned starting materials, and water or an organic solvent may be used as the reaction solvent. As the organic solvent, the solvents same as those used in the above-mentioned first production method can be used. Not to mention it, these reaction solvents may be used alone or two or more of them may be used in form of a mixture.

The condition at the time of reaction of the starting materials is not particularly limited and may be properly adjusted in accordance with the advancing state of the reaction; however, for example, the reaction temperature is adjusted to be preferably 0° C. to 200° C. It is more preferably 30° C. to 170° C. and even more preferably 50° C. to 150° C. The reaction time is adjusted to be preferably 0.2 hours to 200 hours, more preferably 0.5 hours to 150 hours, and even more preferably 1 hour to 100 hours.

According to the third production method of the invention using the above-mentioned TMSCN, amine and/or ammonium salt, and boron compound as starting materials, an ionic compound having tetracyanoborate ion ($[B(CN)_4]^-$) is obtained at a further higher yield than that in the case of using an alkali metal cyanide as the CN source, or that in the case of using TMSCN and an alkali metal-containing boron compound as starting materials.

The ionic compound obtained by the third production method of the invention has the structure defined by the above-mentioned general formula (I), and comprises an organic cation or an inorganic cation as the cation $[Kt]^{m+}$ and $[B(CN)_4]^-$ as the anion. The cation $[Kt]^{m+}$ may be derived from the boron compound (e.g. an alkali metal ion), or from the ammonium salt (e.g. one of ammonium cations defined by the above-mentioned general formulas (VII) to (IX)), or an organic cation or an inorganic cation different from them.

[Fourth Production Method]

Next, the fourth production method will be described. The fourth method for producing an ionic compound of the invention is characterized in that reaction of hydrogen cyanide, an amine, and a boron compound is carried out to obtain an ionic compound defined by the following general formula (I).

[Chemical Formula 23]

(I)

(wherein $[Kt]^{m+}$ denotes an organic cation $[Kt^b]^{m+}$ or an inorganic ion $[Kt^a]^{m+}$; and m denotes an integer of 1 to 3).

To synthesize the ionic compound containing tetracyanoborate ion, the inventors have found that use of hydrogen cyanide in place of an alkali metal cyanide such as potassium cyanide or trimethylsilyl cyanide which has been used conventionally as a cyanide (CN) source makes it possible to economically obtain an ionic compound defined by the above-mentioned general formula (I).

Although not clearly understanding the reason why the ionic compound containing tetracyanoborate can be obtained quickly by using hydrogen cyanide, an amine and a boron compound, the inventors of the invention suppose the reason as follows. In the reaction system, at first hydrogen atom of hydrogen cyanide, which is a starting material, is coordinated with lone pair electron of nitrogen of the amine to form an ammonium complex. Next, the ammonium complex and the boron compound are supposedly reacted to produce the ionic compound containing TCB as a result. That is, in the complex formed from hydrogen cyanide and an amine, the bond between N—CN is relatively weak as compared with that of an alkali metal cyanide, which has been used as a cyanide source. Accordingly, it is supposed that if hydrogen cyanide and an amine are used as starting materials, free cyanide ion can be formed easily in the reaction system and as a result, the ionic compound containing TCB is quickly produced.

The organic cation $[Kt]^{m+}$ comprising the ionic compound $Kt[B(CN)_4]_m$ obtained by the production method of the invention includes those derived from the cations contained in boron compounds; those derived from ammonium generated from hydrogen cyanide and amines; and also those derived from cations composing ionic substances to be employed for cation exchange reaction described later.

<Hydrogen Cyanide>

As described above, in the fourth production method of the invention, hydrogen cyanide is used as a cyanide source. Hydrogen cyanide may be a gas or a liquid and may be used in form of a solution obtained by dissolving hydrogen cyanide in water or an organic solvent. In this connection, because of handling convenience, liquid or solution type hydrogen cyanide is preferable to be used.

<Amine>

Next, an amine will be described. In the fourth production method, an amine is used as a starting material. An amine usable in the invention is preferably amines defined by the above-mentioned general formula (XII) and concrete examples of the amine include amines same as those used in the third production method.

<Boron Compound>

In the fourth production method, starting materials containing the above-mentioned hydrogen cyanide, amine, and boron compound are reacted to synthesize an ionic compound defined by the above-mentioned general formula (I). The above-mentioned boron compound is not particularly limited as long as it is a compound containing boron and those same as the boron compounds usable in the above-mentioned first production method can be used.

In the fourth production method, the above-mentioned hydrogen cyanide, amine, and boron compound are reacted to synthesize an ionic compound defined by the above-mentioned general formula (I). The mixing embodiment of the starting materials is not particularly limited and an embodiment that hydrogen cyanide, an amine, and a boron compound are loaded to a reaction container and an embodiment that hydrogen cyanide and an amine are previously loaded to a reaction container and thereafter, the boron compound is added to the reaction system can be employed.

The mixing ratio of the amine to hydrogen cyanide is preferably 0.02:1 to 50: 1 (hydrogen cyanide:amine, mol ratio). It is more preferably 0.05:1 to 20:1 and even more preferably 0.1:1 to 10:1. If the mixing amount of hydrogen cyanide is too low the production amount of the desired ionic compound may possibly be low or byproducts (e.g. tricyanoborate, dicyanoborate, etc.) may be produced in some cases. On the other hand, if the mixing amount of hydrogen cyanide is too high, the amount of impurities derived from CN is increased and it tends to be difficult to refine the desired product.

The mixing ratio of the boron compound to hydrogen cyanide is preferably 1:4 to 1:100 (boron compound: hydrogen cyanide, mol ratio). It is more preferably 1:4 to 1:50 and even more preferably 1:4 to 1:20. If the mixing amount of boron compound is too low the production amount of the aimed ionic compound may possibly be low in some cases. On the other hand, if the mixing amount of boron compound is too high, the amount of impurities derived from the boron compound is increased and it tends to be difficult to refine the desired product.

In the fourth method for producing an ionic compound of the invention, to evenly promote the reaction, it is preferable to use a reaction solvent. The reaction solvent is not particularly limited as long as it can dissolve the above-mentioned starting materials, and water or an organic solvent may be used as the reaction solvent. The organic solvent may be same as those exemplified in the first production method. Needless to say, the above-mentioned reaction solvents may be used alone or two or more of them may be used in form of a mixture.

The condition at the time of reaction of the starting materials is not particularly limited and may be properly adjusted in accordance with the advancing state of the reaction; however, for example, the reaction temperature is adjusted to be preferably 30° C. to 250° C. It is more preferably 50° C. to 170° C. and even more preferably 80° C. to 150° C. The reaction time is adjusted to be preferably 0.2 hours to 200 hours, more preferably 0.5 hours to 150 hours, and even more preferably 1 hour to 100 hours.

According to the fourth production method of the invention in which hydrogen cyanide is used as a CN reagent, an ionic compound having tetracyanoborate ion ($[B(CN)_4]^-$) can be obtained economically as compared with conventional methods of using an alkali metal cyanide and trimethylsilyl cyanide.

<Cation-Exchange Reaction>

The ionic compound obtained by the production method of the invention may be subjected further to cation-exchange reaction. As described below, since the characteristics of the ionic compound of the invention depend on the cation type, an ionic compound with different characteristics can be obtained easily by carrying out cation exchange reaction.

As described in the first production method, if an ionic substance $KtX^b$ ($[Kt]^{m+}$ denotes an organic cation or an inorganic cation; $[X^b]^{m-}$ denotes an anion; and m denotes an integer of 1 to 3) is used as a starting material, an ionic compound having a desired cation can be obtained without additional performance of cation-exchange reaction. These embodiments are also one of recommended embodiments of the invention.

Accordingly, with respect to the ionic compound of the invention defined by the above-mentioned general formula (I), in the case no cation-exchange reaction is carried out, the cation $[Kt]^{m+}$ may be cations derived from boron compounds and or cations derived from cyanides $M^a(CN)_n$ (first production method); cations derived from ammonium cyanide compounds, that is, cations of various derivatives having structures defined by the above-mentioned general formulas (VII) to (IX) (second production method); cations derived from ammonium salts (third production method); and ammonium cations produced from hydrogen cyanide and amines (fourth production method).

On the other hand, in the case the above-mentioned each reaction is carried out in presence of an ionic substance and, in the case the cation-exchange reaction of the obtained ionic compound is carried out after the above-mentioned reaction, the cation becomes the cation $[Kt]^{m+}$ composing the ionic substance $KtX^b$, that is a conventionally known organic cation or an inorganic cation $[Kt]^{m+}$ such as an alkali metal ion, and an alkaline earth metal ion.

With respect to $[Kt]^{m+}$ comprising the ionic substance, ammonium defined by the above-mentioned general formula $[N^+—(R)_4]$ is preferable as an organic cation and alkali metal ions such as $Li^+$, $Na^+$ and $K^+$ and alkaline earth metal ions such as $Mg^{2+}$ and $Ca^{2+}$ are preferable as an inorganic metal cation. More preferable cations are onium cations defined by the above-mentioned general formulas (III) to (V) and ammonium type compound derivatives defined by the above-mentioned general formulas (VII) to (IX).

On the other hand, preferable examples of the anion $[X^b]^{m-}$ include a halide ion, cyanide ion ($CN^-$), hydroxy ion ($OH^-$), cyanate ion ($OCN^-$), thiocyanate ion ($SCN^-$), an alkoxy ion ($RO^-$), sulfate ion, nitrate ion, acetate ion, carbonate ion, perchlorate ion, an alkylsulfate ion, an alkylcarbonate ion, etc. Among these ions, a halide ion is preferable and $Cl^-$ or $Br^-$ is particularly preferable.

That is, those obtained by combining the above-mentioned $[Kt]^{m+}$ and $[X^b]^{m-}$ are preferably employed as the ionic substance $KtX^b$ and particularly preferable examples include salts of alkyl quaternary ammonium and halide ion such as tetrabutylammonium fluoride, tetrabutylammonium chloride, tetrabutylammonium bromide, tetraethylammonium fluoride, tetraethylammonium chloride, tetraethylammonium bromide, triethylmethylammonium fluoride, triethylmethylammonium chloride, and triethylmethylammonium bromide; salts of alkyl tertiary ammonium and halide ion such as triethylammonium fluoride, triethylammonium chloride, triethylammonium bromide, dibutylmethylammonium fluoride, dibutylmethylammonium chloride, dibutylmethylammonium bromide, dimethylethylammonium fluoride, dimethylethylammonium chlorides and dimethylethylammonium bromide; salts of imidazolium and halide ion such as 1-ethyl-3-methylimidazolium fluoride, 1-ethyl-3-methylimidazolium chloride, 1-ethyl-3-ethylimidazolium bromide, 1,2,3-trimethylimidazolium fluoride, 1,2,3-trimethylimidazolium chloride, and 1,2,3-trimethylimidazolium bromide; and salts of pyrrolidinium and halide ion such as N,N-dimethylpyrrolidinium fluoride, N,N-dimethylpyrrolidinium chloride, N,N-dimethylpyrrolidinium bromide, N-ethyl-N-methylpyrrolidinium fluoride, N-ethyl-N-methylpyrrolidinium chloride, and N-ethyl-N-methylpyrrolidinium bromide. Further, as the ionic substance, salts $Kt^a X^b$ of halide ion and alkali metal ion such as $Li^+$, $Na^+$ and $K^+$ may be used. Additionally, in terms of decrease of the amount of impurities derived from F, it is recommended to use those containing no F atom among the above-mentioned ionic substances.

The above-mentioned ionic substances $KtX^b$ may be used alone or two or more of them may be used in combination.

The cation-exchange reaction may be carried out by reacting an ionic compound obtained by the first to fourth production methods of the invention with an ionic substance $KtX^b$ having a desired cation.

In this case, the mixing ratio of the ionic compound $Kt[B(CN)_4]_m$ and the ionic substance $KtX^b$ at the time of the cation-exchange reaction is adjusted to be preferably 50:1 to 1:50 (ionic compound $Kt[B(CN)_4]_m$:ionic substance $KtX^b$, mol ratio). It is more preferably 20:1 to 1:20 and even more preferably 10:1 to 1:10. If the amount of the ionic substance is too low, it may be sometimes difficult to quickly promote the exchange reaction of the organic cation. On the other hand, if an excess amount of the ionic substance is used, the unreacted ionic substance contaminates the product and it tends to be difficult to refine the product.

The exchange reaction of the organic cation may be carried out merely by mixing the ionic compound $Kt[B(CN)_4]_m$ and the ionic substance $KtX^b$ in presence of a solvent and at that time, the temperature may be 0° C. to 200° C. (more preferably 10° C. to 100° C.) and reaction may be carried out for 0.1 hours to 48 hours (more preferably 0.1 hours to 24 hours). Preferably used as the solvent may be organic solvents, for example, ester type solvents such as ethyl acetate, isopropyl acetate, and butyl acetate; ketone type solvents such as 2-butanone and methyl isobutyl ketone; ether type solvents such as diethyl ether, dibutyl ether, and cyclohexyl methyl ether; chlorine type solvents such as dichloromethane and chloroform; aromatic type solvents such as toluene, benzene, and xylene; and aliphatic hydrocarbons such as hexane. These solvents may be used alone or two or more of them may be used in combination. In this connection, use of two or more reaction solvents is one of preferable conditions for the above-mentioned reaction.

<Method for Producing Ionic Compound-treatment with Oxidizing Agent>

The production method of the invention is preferably a method further involving a step of bringing a product (ionic compound) obtained by the above-mentioned first to fourth production methods into contact with an oxidizing agent. In the case the cation-exchange reaction is carried out successively to the first to fourth production methods, the contact of the ionic compound, which is the product, and an oxidizing agent may be carried out before or after the cation-exchange reaction and may be carried out both of before and after the cation-exchange reaction.

As described above, the impure ionic components contained in the ionic compound deteriorate electrochemical devices and their peripheral members for which the ionic compound is employed. Consequently, it may possibly result in decrease of the performance of the electrochemical devices. Further, in the production method of the invention, a cyanide $M^a(CN)_n$ (first production method), an ammonia cyanide (second production method), TMSCN (third production method), and hydrogen cyanide (fourth production method) are used as starting materials. Consequently, free cyanide ion ($CN^-$) or the like derived from starting materials may sometimes remain in the product or impurities inevitably mixed in the production process may possible exist in some cases. The ionic compound of the invention is sometimes used as a constituent material for electrochemical devices and the impurities such as $CN^-$ existing in the ionic compound decreases the ion conductivity and corrodes electrodes to deteriorate the electrochemical capabilities.

Therefore, the inventors of the invention have made investigations to lower the content of these impurities of ionic components in the ionic compound. In general, an organic compound tends to be oxidized and decomposed in the presence of an oxidizing agent and it is supposed that an ionic compound containing tetracyanoborate $[B(CN)_4]^-$ as an anion is also similarly oxidized and decomposed. Accordingly, the impurities of ionic components in the ionic compound are removed in form of an alkali metal salt (NaCN, NaCl) by transferring it to a water layer by extraction treatment using an aqueous NaOH solution or the like; however cyanide ion ($CN^-$) is weakly acidic and the solubility of its salt with an alkali metal in water is not so high and therefore, the extraction efficiently is low. Further, to sufficiently lower the impurity amount, it is needed to repeat the extraction process a plurality of times and it results in a problem that the yield of the ionic compound is lowered.

Nevertheless, the inventors of the invention have found that the ionic compound containing TCB as an anion unexpectedly has higher stability than common organic compounds to an oxidizing agent, and therefore, excess cyanide ion ($CN^-$) contained in the product can be decomposed by bringing the ionic compound into contact with an oxidizing agent after the synthesis. Moreover, the content of impurities inevitably mixed in the starting materials and in the synthesis process can be lowered.

Especially, in the case the product obtained by reaction of trimethylsilyl cyanide and a boron compound and an oxidizing agent are brought into contact with each other, a highly pure ionic compound with lowered impurities such as silicon and halide ions and water is obtained.

<Treatment with Oxidizing Agent>

Examples of an oxidizing agent to be used for the above-mentioned treatment with an oxidizing agent may be peroxides such as hydrogen peroxide, sodium perchlorate, peracetic acid, and meta-chloroperbenzoic acid (mCPBA); manganese compounds such as potassium permanganate and manganese oxide; chromium compound such as potassium dichromate; halogen-containing compounds such as potassium chlorate, sodium bromate, potassium bromate, sodium hypochlorite, and chlorine dioxide; inorganic nitrogen compounds such as nitric acid and chloramine; acetic acid, and osmium tetraoxide. Among these compounds, peroxides are preferable and hydrogen peroxide and sodium perchlorate are more preferable. Especially, in the case of using hydrogen peroxide as the oxidizing agent, impurities such as chloride ion ($Cl^-$) and cyanate ion ($NCO^-$) are efficiently distributed in the hydrogen peroxide-aqueous layer and the extraction efficiency of the ionic compound is improved and therefore it is particularly preferable. Furthermore, in the case of using hydrogen peroxide, those absorbing moisture and components easy to be hydrated among impurities are efficiently distributed in the hydrogen peroxide-aqueous layer and therefore, the purity of the ionic compound is increased and at the same time, the water content is also easily decreased in the ionic compound.

The oxidizing agent may be in solid state or liquid state, and in the case of solid state, it may be dissolved in a solvent. An oxidizing agent solution obtained by dissolving a liquid-state oxidizing agent or a solid-state oxidizing agent in a solvent may be used after being further diluted.

Although it depends on the impurity amount (especially, $CN^-$ or the like) in the crude ionic compound, the use amount of the oxidizing agent is preferably 1 part by weight to 1000 parts by weight, more preferably 10 parts by weight to 500 parts by weight, further more preferably 20 parts by weight to 300 parts by weight, and even more preferably 50 parts by weight to 100 parts by weight per 100 parts by weight of the crude ionic compound. Additionally, in the case that the oxidizing agent amount is too high, the ionic compound may possibly be decomposed. On the other hand, if the oxidizing agent amount is too low, it is difficult to sufficiently lower the excess ionic components and impurities in some cases. In this connection, "crude ionic compound" means the component obtained by removing a solvent from a reaction solution after the synthesis. The treatment with an oxidizing agent may be carried out without removal of the reaction solvent or the like after the synthesis or after other refining treatment described below.

The treatment with an oxidizing agent is not particularly limited as long as the crude ionic compound and an oxidizing agent are brought into contact with each other, and the crude ionic compound after synthesis as it is may be brought into contact with an oxidizing agent, or a solution of the crude ionic compound is prepared and the obtained crude ionic compound solution may be mixed with an oxidizing agent for the contact. That is, a contact embodiment may include an embodiment that a solid-state oxidizing agent is added to the crude ionic compound solution to bring both into contact with each other; an embodiment that the crude ionic compound solution and an oxidizing agent solution are mixed to bring both into contact with each other; and an embodiment that the crude ionic compound in solid state is added to a oxidizing agent solution to bring both into contact with each other. Additionally, a solvent for dissolving the crude ionic compound is preferably a solvent to be used for treatment with activated carbon described below.

As described above, the ionic compound of the invention has high tolerability to an oxidizing agent as compared with common organic substances; however excess contact with an oxidizing agent becomes a cause of decomposition of the ionic compound. Consequently, in terms of suppression of decomposition of the ionic compound, it is recommended to carry out the treatment with an oxidizing agent at low temperature within a short time. For example, the treatment with an oxidizing agent is carried out preferably at a temperature equal to or lower than the reaction temperature at the time of synthesizing the ionic compound, and more preferably at a temperature equal to or lower than the boiling temperature of the solvent. Concretely, it is preferably 0° C. to 150° C., more preferably 0° C. to 130° C., furthermore preferably 10° C. to 100° C., and even more preferably 10° C. to 80° C.

<Other Refining Methods>

In the production method of the invention, to further decrease the impurity amount in the ionic compound, conventionally known refining methods other than the above-mentioned treatment with an oxidizing agent may be employed. Examples of conventionally known refining methods may include washing with water, an organic solvent, and their mixed solvent; an adsorption purification method; a re-precipitation method; a separatory extraction method; a re-crystallization method; a crystallization method; and chromatography. These refining methods may be carried in combination.

In the case the above-mentioned another refining method is employed in combination, the timing conducting the another refining method is not particularly limited and any of the following embodiments may be employed: before contact of the crude ionic compound and an oxidizing agent; after contact of the crude ionic compound and an oxidizing agent; and both before and after contact of the crude ionic compound and an oxidizing agent.

For example, in the case an adsorption purification method is employed, examples of an adsorbent may include activated carbon, silica gel, alumina, zeolites, and the like. Among them, adsorption treatment using activated carbon as an adsorbent (treatment with activated carbon) is preferable since contamination of the ionic compound with impurities is little.

The activated carbon usable for the adsorption treatment is not particularly limited. The shape of the activated carbon is not particularly limited as long as it has a wide surface area and may include powder-like, milled, granulated, pelletized, and spherical shapes and among these shapes, a powder-like activated carbon is preferable to be used because of a wide surface area. Further, the activated carbon is preferably those having a surface area of 100 $m^2/g$ or higher, more preferably those having a surface area of 400 $m^2/g$ or higher, and even more preferably those having a surface area of 800 $m^2/g$ or higher. To avoid contamination of the ionic compound with impurities contained in the activated carbon, it is preferable to employ activated carbon with little impurity content and one example of such an activated carbon is Carborafin (registered trade name)-6 manufactured by Japan EnviroChemicals, Ltd.

The use amount of the activated carbon is preferably not less than 1 part by weight and not more than 500 parts by weight; more preferably not less than 10 parts by weight and not more than 300 parts by weight; and even more preferably not less than 20 parts by weight and not more than 200 parts by weight per 100 parts by weight of the crude ionic compound.

The treatment with activated carbon is preferably carried out for the crude ionic compound immediately after synthesis and before the treatment with an oxidizing agent. From a viewpoint that the effect of the treatment with activated carbon is caused efficiently, it is recommended that the crude ionic compound is subjected to the treatment with activated carbon while being dissolved or dispersed in a solvent.

A solvent usable for the treatment with activated carbon is not particularly limited; however a solvent in which the crude ionic compound can be dissolved is preferable. Examples include water; aliphatic mono-alcohols such as methanol, ethanol, n-propyl alcohol, isopropyl alcohol, 1-butanol, sec-butanol, tert-butanol, 1-pentanol, 2-pentanol, 3-pentanol, 3-methyl-1-butanol, 3-methyl-2-butanol, 2-methyl-1-butanol, tert-amyl alcohol, neopentyl alcohol, 1-hexanol, 2-hexanol, 3-hexanol, 2-methyl-1-pentanol, 3-methyl-3-pentanol, 4-methyl-2-pentanol, 3,3-dimethyl-2-butanol, 1-heptanol, 2-heptanol, 3-heptanol, 2-methyl-3-hexanol, 2,4-dimethyl-3-pentanol, 1-octanol, 2-octanol, 3-octanol, 2-ethyl-nonanol, 2,4,4-trimethyl-1-pentanol, 1-nonanol, 2-nonanol, 2,6-dimethyl-4-heptanol, 3,5,5-trimethyl-1-hexanol, 1-decanol, 2-decanol, 4-decanol, and 3,7-dimethyl-1-octanol; alicyclic mono-alcohols such as cyclopentanol and cyclohexanol; polyhydric alcohols such as ethylene glycol, propylene glycol, 1,4-butanediol, 1,4-dihydroxy-2-butene, 1,2-dihydroxy- 3-butene, and glycerin; ketones such as acetone, methyl ethyl ketone, methyl butyl ketone, methyl isobutyl ketone, and methyl isopropyl ketone; ethers such as dimethyl ether, diethyl ether, dipropyl ether, methyl-tert-butyl ether, butyl ethyl ether, dibutyl ether, dipentyl ether, tetrahydrofuran, and tetrahydropyran; esters such as methyl acetate, ethyl acetate, isopropyl acetate, butyl acetate, methyl acrylate, and methyl methacrylate; straight or branched aliphatic saturated hydrocarbons such as n-pentane, n-hexane, methylpentane, n-heptane, methylhexane, dimethylpentane, n-octane, methylheptane, dimethylhexane, trimethylpentane, dimethylheptane, and n-decane; straight or branched aliphatic unsaturated hydrocarbons such as 1-pentene, 1-hexene, 4-methyl-1-pentene, and 1-heptene; aromatic hydrocarbons such as benzene, toluene, xylene, ethylbenzene, and propylbenzene; alicyclic compounds such as cyclopentane, methylcyclopentane, cyclohexane, methylcyclohexane, dimethylcyclohexane, ethylcyclohexane, and propylcyclohexane; halogen-containing solvents such as chloromethane, dichloromethane, trichloromethane, tetrachloromethane, dichloroethylene, trichloroethylene, and tetrachloroethylene; and nitriles such as acetonitrile, propionitrile, butyronitrile, valeronitrile, hexanenitrile, and benzonitrile. Among them, water, ketones, ethers, esters, aliphatic saturated hydrocarbons, and halogen-containing solvents are usable. Further, among them, water, methyl ethyl ketone, dimethyl ether, diethyl ether, butyl acetate, and hexane are preferable. The above-mentioned solvents may be used alone or two or more of them may be used preferably while being mixed. In addition, water to be used for the treatment with activated carbon is preferably ultrapure water (ion resistance of 1.0 Ω·cm or higher) treated by an ultrapure water apparatus equipped with various kinds of filters such as a filter, an ion exchange membrane and a reverse osmosis membrane.

The use amount of a solvent to be used for the treatment with activated carbon is preferably not less than 10 parts by weight and not more than 2000 parts by weight; more preferably not less than 100 parts by weight and not more than 1000 parts by weight; and even more preferably not less than 200 parts by weight and not more than 1000 parts by weight per 100 parts by weight of the crude ionic compound. In the case the solvent amount is too high, the reaction apparatus becomes large and it costs high and moreover, the yield tends to be lowered and thus it is economically disadvantageous. On the other hand, in the case the use amount of the solvent is too low the purity of the ionic compound is sometimes decreased. The ionic compound solution after the treatment with activated carbon may be subjected as it is to the treatment with an oxidizing agent.

As described above, it is one of preferred embodiments of the invention that the crude ionic compound obtained in a syntesis is subjected to the treatment with an oxidation agent and followed by the treatment with activated carbon. Further, after the treatment with an oxidizing agent, other refining methods described above may be employed and it is preferable to carry out washing with water, an organic solvent or their mixed solvent, or separatory extraction.

A solvent to be used in this case is preferably a solvent which can form 2-layer state with a solvent exemplified in the above-mentioned treatment with activated carbon. For example, in the case an organic solvent is used in the treatment with activated carbon, water is preferable to be used for washing and separatory extraction. Use of water makes it possible to efficiently extract the alkali metal ion and the halide ion and remove these ionic components from the ionic compound. Additionally, in terms of layer separation from water and recovery efficiency of the ionic compound, a combination of preferable extraction solvents include combinations of water/hexane, water/methyl ethyl ketone, water/methyl isobutyl ketone, water/dimethyl ether, water/diethyl ether, water/ethyl acetate, water/butyl acetate, and water/dichloromethane; and among them, more preferable combinations are water/ethyl acetate, water/butyl acetate, water/methyl isobutyl ketone, and water/diethyl ether, and even more preferable combinations are water/ethyl acetate, water/butyl acetate, and water/diethyl ether.

According to the invention employing the above-mentioned treatment with an oxidizing agent, an ionic compound with a high purity and a low content of impure ionic components is obtained.

<Uses>

The ionic compound $Kt[B(CN)_4]_m$ of the invention has one characteristic that it is in liquid-phase at 100° C. or lower and becomes an ionic liquid by selecting the cation $[Kt]^{m+}$. Accordingly, the ionic compound of the invention obtained by the above-mentioned production method is preferably usable as a material composing electrochemical devices such as primary batteries and batteries having charge/discharge mechanism, e.g., lithium (ion) secondary batteries and fuel cells, and also electrolytic capacitors, electric double layer capacitors, solar cells, electrochromic display devices, and electrochemical gas sensors.

Further, in general, since an ionic liquid has a characteristic that it is a liquid having an ionic bond, it is known that the ionic liquid has high electrochemical and thermal stability and also has a property of selectively absorbing a specific gas such as carbon dioxide, and the ionic compound obtained by the production method of the invention also has characteristics same as described above.

Consequently, as uses of the ionic compound of the invention other than the above-mentioned electrochemical material uses, the ionic compound can be used preferably for various uses, e.g., as a repeatedly usable reaction solvent for organic synthesis and a sealing agent and a lubricant for mechanical movable parts based on the high thermal stability; as a conductivity supplying agent for polymers based on both of the electrochemical property and thermal stability; as a gas absorbent for carbon dioxide or the like based on the gas-absorbing property; etc.

Next, a case of using the ionic compound of the invention as an ion-conductive material for the above-mentioned electrochemical devices will be described.

[Ion Conductive Material]

As described above, the ionic compound of the invention contains tetracyanoborate defined by $[B(CN)_4]^-$ as an anion and the invention includes an ion-conductive material containing an ionic compound having an anion defined by the following general formula (XVI) other than the above-mentioned anion.

[Chemical Formula 24]

$$(NC)_v-X^{d-} \qquad \qquad (XVI)$$

(in the formula (XVI), $X^d$ denotes at least one element selected from Al, Si, P, Ga, and Ge; and v is an integer of 4 to 6).

The ion-conductive material of the invention contains the ionic compound having, as an anion component, tetracyanoborate or tetracyanoborate together with an anion defined by the above-mentioned general formula (XVI), and it is preferable that the above-mentioned anion component has the highest occupied molecular orbital energy level of −5.5 eV or lower which is caluculated by employing a molecular orbital computation method.

Investigations of an ion-conductive material by employing a computational chemical technique are made in Journal of The Electrochemical Society, 149 (12) A1572-A1577 (2002) and here, as an index for obtaining a compound with high withstand voltage, the highest occupied molecular orbital energy levels of various kinds of anions are calculated by employing a molecular orbital computation method. This document reports $PF_6^-$ and $AsF_6^-$ as anions having low highest occupied molecular orbital energy levels and wide potential windows. However, compounds containing these anions have problems; that is, fluorine atoms contained in the structure are isolated with lapse of time, and corrode electrodes, or react on a trace of water contained in the system and generate harmful hydrogen fluoride gas, or As itself is toxic. On the other hand, the ionic compound of the invention has a decreased content of impurities such as fluorine atoms as described above and contains no As in the structure or in the synthesis process, so that a problem of electrode corrosion or the like is hardly caused. Further, the anion component of the invention has the highest occupied molecular orbit energy level same as those of $PF_6^-$ and $AsF_6^-$, and has a wide potential window, so that it can be used preferably as an ion conductor.

In the above-mentioned formula (XVI), v is an integer of 4 to 6 and determined based on the valence of the element X. For example, in the case X is Al or Ga, v=4 and in the case X is Si or Ge, v=5. Further, in the case X is P, v=6. A preferable embodiment of the ion-conductive material of the invention has an ionic compound having tetracyanoborate and/or the anion component defined by the above-mentioned general formula (XVI) essentially. The anion component is preferably tetracyanoborate and an anion defined by the general formula (XVI) in which X is Al and v=4 and tetracyanoborate is most preferable as the anion component.

The highest occupied molecular orbital energy level of the anion component (tetracyanoborate and the anion component defined by the general formula (XVI)) contained in the ion-conductive material of the invention, which is calculated by employing a molecular orbital computation method, is preferably −5.5 eV or lower, more preferably −5.6 eV or lower, and even more preferably −5.7 eV or lower.

Further, in terms of corrosiveness and harmfulness, the above-mentioned ion-conductive material is preferably those which contain no F atom and no As in the composition. Furthermore, for the same reason, the ion-conductive material is preferably those which contain no Sb. In addition, the above-mentioned ion-conductive material may contain only one kind of anion component and also may contain two or more kinds of anion components.

The cation contained in the ion-conductive material of the invention is not particularly limited and may be either an organic cation or an inorganic cation, as long as it can form a salt with tetracyanoborate and the anion defined by the general formula (XVI); however an onium cation is preferable. Examples of the onium cation are onium cations defined by (III) to (V). In this case, preferable uses of the ion-conductive material are electric double layer capacitors, electrolytic capacitors, etc.

In the case the above-mentioned ion-conductive material is used as a material of an electrolyte solution of an electric double layer capacitor or an electrolytic capacitor, the amount of the ion-conductive material is preferably 1 weight % or higher and 99.5 weight % or lower in 100 weight % of the material of an electrolyte solution. It is more preferably 5 weight % or higher and 95 weight % or lower and even more preferably 10 weight % or higher and 90 weight % or lower.

As described above, the ionic compound and the ion-conductive material of the invention can work as an electrolyte composing an electrolyte solution or a solid electrolyte in an ion conductor which various kinds of electrochemical devices comprise. In addition, these electrolyte solution and solid electrolyte may contain other electrolyte salts in addition to the ion-conductive material of the invention.

As other electrolyte salts, electrolytes containing ions as carriers may be used, and one or more of electrolytes can be used. It is preferable that the dissociation constant in an electrolyte solution or a polymer solid electrolyte is high, and preferable examples include alkali metal salts and alkaline earth metal salts of trifluoromethane sulfonic acid such as $LiCF_3SO_3$, $NaCF_3SO_3$, and $KCF_3SO_3$; alkali metal salts and alkaline earth metal salts of perfluoroalkanesulfonic acid imide such as $LiC(CF_3SO_2)_3$, $LiN(CF_3CF_2SO_2)_2$, and $LiN(FSO_2)_2$; alkali metal salts and alkaline earth metal salts of hexafluorophosphoric acid such as $LiPF_6$, $NaPF_6$, and $KPF_6$; alkali metal salts and alkaline earth metal salts of perchloric acid such as $LiClO_4$ and $NaClO_4$; tetrafluoroboric acid salts such as $LiBF_4$ and $NaBF_4$; alkali metals salts such as $LiAsF_6$, LiI, NaI, $NaAsF_6$, and KI; quaternary ammonium salts of perchloric acid such as tetraethylammonium perchlorate; quaternary ammonium salts of tetrafluoroboric acid such as $(C_2H_5)_4NBE_4$; quaternary ammonium salts such as $(C_2H_5)_4NPF_6$; and quaternary phosphonium salts such as $(CH_3)_4PBF_4$ and $(C_2H_5)_4P BE_4$. Among them, alkali metal salts and/or alkaline earth metal salts are preferable. Further, in terms of solubility in an organic solvent or ion conductivity, $LiPF_6$, $LiBF_4$, $LiAsF_6$, alkali metal salts and alkaline earth metal salts of perfluoroalkanesulfonic acid imide, and quaternary ammonium salts are preferable. As the alkali metal salts, lithium salts, sodium salts, and potassium salts are preferable and as the alkaline earth metal salts, calcium salts and magnesium salts are preferable. Lithium salts are more preferable.

The used amount of above-mentioned other electrolytic salts is preferably 0.1 weight % in the lower limit and 50 weight % in the upper limit to the total 100 weight % of the ion-conductive material of the invention and other electrolytic salts. If it is less than 0.1 weight %, the absolute amount of ions may become insufficient and ion conductivity may possibly become low and if it exceeds 50 weight %, the mobility of ions may significantly be inhibited. The upper limit is more preferably 30 weight %.

Uses of the ion-conductive material of the invention may be, for example, for electrochemical devices such as electrolytic capacitors, electric double layer capacitors, lithium ion capacitors, solar cells, and electrochromic display devices besides primary batteries and batteries having charge/discharge mechanism, e.g., lithium (ion) secondary batteries and fuel cells. In general, these devices have, as basic constituent elements, an ion conductor, a negative electrode, a positive electrode, current collectors, a separator, and a container.

As the above-mentioned ion conductor, a mixture of an electrolyte and an organic solvent is preferable. If an organic solvent is used, the ion conductor is called generally as an electrolyte solution.

As the organic solvent, a non-protonic solvent in which the above-mentioned ion-conductive material can be dissolved may be used. The non-protonic solvent is preferably those having good compatibility with the ion-conductive material of the invention and high dielectric constant as well as high solubility for other electrolytic salts, boiling point of 60° C. or higher, and a wide range of electrochemical stability. The non-protonic solvent is more preferably organic solvents with low water content (non-aqueous solvent). Examples of such solvent include ethers such as 1,2-dimethoxyethane, tetrahydrofuran, 2-methyltetrahydrofuran, crown ether, triethylene glycol methyl ether, tetraethylene glycol dimethyl ether, and dioxane; carbonates such as ethylene carbonate, propylene carbonate, diethyl carbonate, and methyl ethyl carbonate; aliphatic carbonic acid esters such as dimethyl carbonate, ethyl methyl carbonate, diethyl carbonate, diphenyl carbonate, and methyl phenyl carbonate; cyclic carbonate esters such as ethylene carbonate, propylene carbonate, ethylene 2,3-dimethylcarbonate, butylene carbonate, vinylene carbonate, and ethylene 2-vinylcarbonate; aliphatic carboxylic acid esters such as methyl formate, methyl acetate, propionic acid, methyl propionate, ethyl acetate, propyl acetate, butyl acetate, and amyl acetate; aromatic carboxylic acid esters such as methyl benzoate and ethyl benzoate; carboxylic acid esters such as γ-butyrolactone, γ-valerolactone, and δ-valerolactone; phosphoric acid esters such as trimethyl phosphate, ethyl dimethyl phosphate, diethyl methyl phosphate, and triethyl phosphate; nitriles such as acetonitrile, propionitrile, butyronitrile, valeronitrile, hexanenitrile, benzonitrile, methoxypropionitrile, glutaronitrile, adiponitrile, and 2-methylglutaronitrile; amides such as N-methylformamide, N-ethylformamide, N,N-dimethylformamide, N,N-dimethylacetamide, N-methylpyrrolidinone, N-methylpyrrolidone, and N-vinylpyrrolidone; sulfur compounds such as dimethylsulfone, ethylmethylsulfone, diethylsulfone, sulfolane, 3-methylsulfolane, and 2,4-dimethylsulfolane; alcohols such as ethylene glycol, propylene glycol, ethylene glycol monomethyl ether, and ethylene glycol monoethyl ether; ethers such as ethylene glycol dimethyl ether, ethylene glycol diethyl ether, 1,4-dioxane, 1,3-dioxolane, tetrahydrofuran, 2-methyltetrahydrofuran, 2,6-dimethyltetrahydrofuran, and tetrahydropyrane; sulfoxides such as dimethyl sulfoxide, methyl ethyl sulfoxide, and diethyl sulfoxide; aromatic nitriles such as benzonitrile and tolunitrile; nitromethane, 1,3-dimethyl-2-imidazolidinone, 1,3-dimethyl-3,4,5,6-tetrahydro-2(1H)-pyrimidinone, 3-methyl-2-oxazolidinone, etc., and preferably these solvents can be used individually or in combination. Among these solvents, carbonic acid esters, aliphatic esters, and ethers are more preferable; and carbonates such as ethylene carbonate, and propylene carbonate, and γ-butyrolactone, γ-valerolactone are even more preferable.

The concentration of the electrolyte in the above-mentioned ion conductor is preferably 0.01 mol/dm$^3$ or higher and not higher than the saturated concentration. If it is lower than 0.01 mol/dm$^3$, the ion conductivity is low and therefore, it is not preferable. It is more preferably 0.1 mol/dm$^3$ or higher and 2.5 mol/dm$^3$ or lower.

In the case the ion-conductive material of the invention is used as an electrolyte of a lithium ion battery, it is preferable to dissolve the ion-conductive material in two or more kinds of non-protonic solvents. In this case, it is preferable to prepare an electrolyte solution by dissolving the ion-conductive material in a mixed solvent of a non-protonic solvent with a dielectric constant of 20 or higher and a non-protonic solvent with a dielectric constant of 10 or lower among the above-mentioned organic solvents.

In the case the ion-conductive material of the invention is dissolved in the above-mentioned non-protonic solvent, for example, propylene carbonate to obtain an electrolyte solution, the ion conductivity at 25° C. is preferably 0.5 mS/cm or higher in a concentration of 1 mol/L. If the ion conductivity at 25° C. is lower than 0.5 mS/cm, the ion conductor obtained by using the ion-conductive material of the invention is hard to keep excellent ion conductivity for a long time and is difficult to work stably in some cases. It is more preferably 1.0 mS/cm or higher.

The ion-conductive material of the invention is preferable to have withstand voltage of 4 V to 500 V on the bases of Ag/Ag$^+$. It is more preferably 5 V to 500 V. As described above, it is possible to show high withstand voltage by containing an anion having highest occupied molecular orbital energy level of −5.5 eV or lower calculated by employing the molecular orbital computation method.

Hereinafter, (1) a lithium secondary battery, (2) an electrolyte capacitor, (3) an electric double layer capacitor, and (4) a lithium ion capacitor among the electrochemical devices using the ion conductor of the invention will be described more in detail.

(1) Lithium Secondary Battery

A lithium secondary battery comprises a positive electrode, a negative electrode, a separator inserted between the positive electrode and the negative electrode, and an ion conductor obtained by using the ion-conductive material of the invention as basic constituent elements. In this case, the material for an electrolyte solution of the invention contains a lithium salt as an electrolyte. Such a lithium secondary battery is preferably a non-aqueous electrolytic lithium secondary battery, which is a lithium secondary battery containing an electrolyte other than a water-based electrolyte. This lithium secondary battery employs coke as a negative electrode active material and a Co-containing compound as a positive electrode active material, and in this lithium secondary battery, at the time of charge, reaction of $C_6Li \rightarrow 6C+Li+e$ is caused at the negative electrode and the electrons (e) generated on the negative electrode surface are transferred to the positive electrode surface in the electrolyte solution by ion conduction, and reaction of $CoO_2+Li+e \rightarrow LiCoO_2$ is caused at the positive electrode surface, and thus electric current flows from the negative electrode to the positive electrode. At the time of discharge, reverse reactions of the reactions at the time of charge are caused and electric current flows from the positive electrode to the negative electrode. In such a manner, electricity is stored or supplied by chemical reactions of ions.

For the above-mentioned negative electrode, conventionally known materials to be used for the negative electrode can be employed without any particular limit and usable examples are carbon materials such as graphite, e.g. natural graphite and artificial graphite, coke, and charcoal of organic material; lithium alloys such as lithium-aluminum alloys, lithium-magnesium alloys, lithium-indium alloys, lithium-thallium alloys, lithium-lead alloys, and lithium-bismuth alloys; and metal oxides and metal sulfides containing one or more of titanium, tin, iron, molybdenum, niobium, vanadium, zinc, etc. Among these substances, metal lithium and carbon materials which can absorb and desorb alkali metal ion are more preferable.

For the above-mentioned positive electrode, conventionally known materials to be used for the positive electrode can be employed without any particular limit and usable examples are lithium-containing transition metal oxides such as $LiCoO_2$, $LiMnNO_2$, $LiFeO_2$, and $LiFePO_4$. The average particle diameter of the positive electrode active material particles is preferably 0.1 to 30 μm.

(2) Electrolytic Capacitor

An electrolytic capacitor comprises a positive electrode foil, a negative electrode foil, a sheet of electrolytic paper as a separator inserted between the positive electrode foil and the negative electrode foil, lead wires, and an ion conductor obtained by using the ion-conductive material of the invention as basic constituent elements. As such an electrolytic capacitor, an aluminum electrolytic capacitor is preferable. Such an aluminum electrolytic capacitor is preferably those containing, as a dielectric, a thin oxide coating (aluminium oxide) formed on the surface of an aluminum foil by electrolytic anodization, which is previously surface-roughened to form fine unevenness by electrolytic etching.

(3) Electric Double Layer Capacitor

An electric double layer capacitor comprises a negative electrode, a positive electrode and an ion conductor obtained by using the ion-conductive material of the invention as a basic constituent part and a preferable embodiment is those obtained by involving an electrolyte solution which is the ion conductor into electrode parts composed of a positive electrode and a negative electrode set face to face.

Preferable examples of the above-mentioned negative electrode are activated carbon, porous metal oxides, porous metals, and conductive polymers. Preferable examples of the above-mentioned positive electrode are activated carbon, porous metal oxides, porous metals, and conductive polymers.

(4) Lithium Ion Capacitor

A lithium ion capacitor is a capacitor based on the principle of a common electric double layer capacitor and using a carbon-based material capable of absorbing lithium ion as a negative electrode material, and is provided with improved energy density by adding lithium ion thereto, and has a structure formed by combining the negative electrode of a lithium ion secondary battery, and the positive electrode of an electric double layer capacitor based on different principles of charge and discharge for the positive electrode and the negative electrode.

Materials for the above-mentioned negative electrode are preferably those which can absorb and desorb lithium ions. Preferable examples of the materials which can absorb and desorb lithium ions are thermally decomposed carbon; coke such as pitch coke, needle coke, and petroleum coke; graphite; glassy carbon; calcined organic polymer, which are obtained by calcining and carbonizing phenol resins, furan resins, and the like at a proper temperature; carbon fibers; carbon materials such as activated carbon; polymers such as polyacetylene, polypyrrole, and polyacene; lithium-containing transition metal oxides or transition metal sulfides such as $Li_4/3Ti_5/3O_4$ and $TiS_2$; metals to be alloyed with alkali metals such as Al, Pb, Sn, Bi, and Si; cubic system intermetallic compounds having lattices in which alkali metals are intercalated such as AlSb, $Mg_2Si$, and $NiSi_2$; and lithium-nitrogen compounds such as $Li_{3.4}G_fN$ (G: a transition metal; f: a real number exceeding 0 and lower than 0.8). One or more of these substances may be used. Among these substances, carbon materials are more preferable.

On the other hand, as the positive electrode, activated carbon, porous metal oxides, porous metals, and conductive polymers are preferable. The ion conductor using the ion-conductive material of the invention forms the electrolyte solution put between the negative electrode and the positive electrode.

EXAMPLES

Hereinafter, the invention will be described more concretely with reference to Examples. However, it is not intended that the invention be limited to the illustrated Examples. Modifications and substitutions to specific process conditions and structures can be made without departing from the spirit and scope of the present invention.

[NMR Measurement]

$^1$H-NMR and $^{13}$C-NMR spectra were measured by using "Unity Plus" (400 MHz) manufactured by Varian and based on the peak intensity of proton and carbon, the structure of each sample was analyzed. "Advance 400 M" (400 MHz) manufactured by Bruker was employed for $^{11}$B—NMR spectra measurement.

The content of impurities containing F atom was measured by the following method. Using d6-DMSO as a solvent, $^{11}$B—NMR measurement was carried out. The area of a peak derived from $B(CN)_4$ at −38 ppm in the obtained $^{11}$B—NMR spectrum was defined as 100 mol % and this area of the peak and the area of another peak (derived from an impurity) were compared relatively to calculate the number of moles of the impurity (mol percentage (mol %)).

[Measurement of Ion Conductivity]

Each ionic compound obtained in the following Examples was dissolved in $_\gamma$-butyrolactone (GBL) to produce an ionic compound solution of 35 weight % concentration.

Using an impedance analyzer ("SI 1260" manufactured by Solartron) and a SUS electrode, the ion conductivity of the ionic compound solution was measured at a temperature of 25° C. by a complex impedance method.

[Measurement of Potential Window]

A 35 weight % ionic compound solution was prepared in the same manner as that in the ion conductivity measurement.

In 25° C. ambient atmosphere, the potential window was measured by a cyclic voltammetry tool ("HSV-100", manufactured by Hokuto Denko Corporation) using a tripolar cell as an electrode. A glassy carbon electrode is used for a working electrode in the tripolar cell; a Pt electrode for an objective electrode; and an Ag electrode for a reference electrode.

[Measurement of Thermal Decomposition Starting Temperature 1]

In an aluminum pan, 10 mg of each ionic compound obtained by the following Synthesis Example was put and elevated temperature at 5° C./min and the temperature when the weight was decreased by 2% from the initial weight was measured with a thermo gravimetry differential thermal analyzer ("EXSTAR 6000 TG/DTA"; manufactured by Seiko Instrument Inc.).

Example 1

In Example 1, a tetracyanoborate-containing ionic compound was synthesized using a cyanide $M^a(CN)_n$ as a starting material.

Synthesis Example 1-1:

Synthesis of Tetrabutylammonium Tetracyanoborate (Bu$_4$NTCB)

A 50 ml flask equipped with a stirring device, a dripping funnel, and a reflux tube was purged with nitrogen and under nitrogen atmosphere at room temperature, 5.1 g (15.8 mmol) of tetrabutylammonium bromide, 9.26 g (78.9 mmol) of zinc (II) cyanide, 10 ml of toluene and 2.8 g (11.2 mmol) of boron tribromide were added and thereafter, the contents were stirred for 2 days while being heated in an oil bath at 130° C. After 2 days, toluene was removed from the flask in reduced pressure to obtain a black solid. After pulverized with a mortar, the obtained solid was put in a beaker equipped with stirring device and 200 ml of chloroform was added twice to extract the product to the chloroform layer. Next, the obtained chloroform solution was transferred to a separatory funnel and washed with 200 ml of water and thereafter, an organic layer was separated and concentrated by an evaporator to obtain an oily crude product. The crude product was refined by column chromatography filled with neutral alumina (developing solvent, a mixed solution of diethyl ether and chloroform) and a fraction containing the product was separately obtained and dried by removing the solvent to obtain tetrabutylammonium tetracyanoborate, as a product (yellow solid, produced amount: 1.4 g (3.9 mmol), yield: 35%, melting point: 90° C.).
$^1$H-NMR (d6-DMSO): δ 3.16 (m, 8H), 1.56 (m, 8H), 1.30 (ddq, J=11 Hz, J=11 Hz, J=7.2 Hz, 8H), 0.92 (t, J=7.2 Hz, 12H)
$^{13}$C-NMR (d6-DMSO): δ 121.9 (m), 57.7 (s), 39.1 (s), 19.4 (s), 13.7 (s)
$^{11}$B—NMR (d6-DMSO) δ −39.6 (s)

Synthesis Example 1-2

Synthesis of 1-ethyl-3-Methylimidazolium Tetracyanoborate EtMeImTCB)

The same operation as that of Synthesis Example 1-1 was carried out except that 3.0 g (15.8 mmol) of 1-ethyl-3-methylimidazolium bromide was used in place of tetrabutylammonium bromide to obtain 1-ethyl-3-methylimidazolium tetracyanoborate (yellow oily material, produced amount: 1.0 g (4.4 mmol), yield: 38%, melting point: 15° C.).
$^1$H-NMR (d6-DMSO) δ 8.41 (s, 1H), 7.34 (d, J=21.6 Hz, 2H), 3.81 (s, 3H), 1.45 (t, J=7.2 Hz, 3H)
$^{13}$C-NMR (d6-DMSO) δ 136.5 (s), 132.2 (m), 122.9 (s), 45.8 (s), 36.8 (s), 15.4 (s)
$^{11}$B—NMR (d6-DMSO) δ −39.6 (s)

Synthesis Example 1-3

Synthesis of Triethylammonium Tetracyanoborate (Et$_3$HNTCB)

The same operation as that of Synthesis Example 1-1 was carried out except that 2.9 g (15.8 mmol) of triethylammonium bromide was used in place of tetrabutylammonium bromide to obtain triethylammonium tetracyanoborate (yellow solid, produced amount: 1.0 g (4.5 mmol), yield: 40%, melting point: 150° C.).
$^1$H-NMR (d6-DMSO) δ 8.83 (s, 1H), 3.10 (q, J=7.2 Hz, 6H), 1.17 (t, J=7.2 Hz, 9H)
$^{13}$C-NMR (d6-DMSO) δ 121.9 (m), 46.0 (s), 8.8 (s)
$^{11}$B—NMR (d6-DMSO) δ −39.6 (s)

Synthesis Example 1-4

Synthesis of Triethylmethylammonium Tetracyanoborate (ET$_3$MeNTCB)

The same operation as that of Synthesis Example 1-1 was carried out except that 3.1 g (15.8 mmol) of triethymethylammonium bromide was used in place of tetrabutylammonium bromide to obtain triethylmmethylammonium tetracyanoborate (yellow solid, produced amount: 1.2 g (5.0 mmol), yield: 45%, melting point: 115° C.).
$^1$H-NMR (d6-DMSO) δ 3.23 (q, J=6.8 Hz, 6H), 2.86 (s, 3H), 1.18 (t, J=6.8 Hz, 9H)
$^{13}$C-NMR (d6-DMSO) δ 122.5 (m), 55.2 (s), 46.2 (s), 7.7 (s)
$^{11}$B—NMR (d6-DMSO) δ −39.6 (s)

Synthesis Example 1-5

Synthesis of Tetraethylammonium Tetracyanoborate (Et$_4$NTCB)

The same operation as that of Synthesis Example 1-1 was carried out except that 3.3 g (15.8 mmol) of tetraethylammonium bromide was used in place of tetrabutylammonium bromide to obtain tetraethylammonium tetracyanoborate (yellow solid, produced amount: 1.1 g (4.5 mmol), yield: 40%).
$^1$H-NMR (d6-DMSO) δ 3.21 (q, J=7.4 Hz, 8H), 1.50 (tt, J=7.4 Hz, 12H)
$^{13}$C-NMR (d6-DMSO) δ 121.9 (m), 51.5 (s), 7.4 (s)
$^{11}$B—NMR (d6-DMSO) δ −39.6 (s)

Synthesis Example 1-6

Synthesis of Tetrabutylammonium Tetracyanoborate (Et$_4$NTCB)

The same operation as that of Synthesis Example 1-1 was carried out except that 4.4 g (15.8 mmol) of tetraethylammonium chloride was used in place of tetrabutylammonium bromide to obtain tetraethylammonium tetracyanoborate (yellow solid, produced amount: 1.6 g (4.5 mmol), yield: 40%, melting point: 90° C.).
The product showed an NMR spectrum and various physical properties similar to those of the product of Synthesis Example 1-1.

Synthesis Example 1-7

Synthesis of Tetrabutylammonium Tetracyanoborate (Bu$_4$NTCB)

A 50 ml flask equipped with a stirring device, a dripping funnel, and a reflux tube was purged with nitrogen and under nitrogen atmosphere at room temperature, 5.1 g (15.8 mmol) of tetrabutylammonium bromide, 9.26 g (78.9 mmol) of zinc (II) cyanide and 11.2 ml (11.2 mmol) of a p-xylene solution of 1.0 M boron trichloride were added and thereafter, the contents were stirred for 2 days while being heated in an oil bath at 150° C. After 2 days, the organic solvent was removed from the flask in reduced pressure to obtain a black solid. After pulverized with a mortar, the obtained solid was put in a beaker equipped with stirring device and 200 ml of chloroform was added twice to extract the product to the chloroform layer. Next, the obtained chloroform solution was transferred to a separatory funnel and washed with 200 ml of water and thereafter, an organic layer was separated and concentrated by an evaporator to obtain an oily crude product. The crude product was refined by column chromatography filled with neutral alumina (developing solvent, a mixed solution of diethyl ether and chloroform) and a fraction containing the product was separately obtained and dried by removing the solvent to obtain tetrabutylammonium tetracyanoborate, as a product (yellow solid, produced amount: 2.4 g (6.8 mmol), yield: 61%, melting point: 90° C.).
The product showed an NMR spectrum and various physical properties similar to those of the product of Synthesis Example 1-1.

Synthesis Example 1-8

A 100 ml three-neck flask equipped with a stirring device, a dripping funnel, and a reflux tube was loaded with 10.4 g (160 mmol) of potassium cyanide, 10.2 g (32 mmol) of tetrabutylammonium bromide, 5.7 g (22.7 mmol) of boron tribromide, and 18.9 g (205 mmol) of toluene at room temperature, and thereafter, the contents were stirred for 7 days while being heated and refluxed in an oil bath at 130° C. After 7 days, toluene was removed from the flask in reduced pressure and 100 ml of chloroform was added thereto and stirred for 30 minutes at room temperature. Next, after the solution was filtered to remove the precipitate, the filtrate was concentrated to obtain an oily crude product. The crude product was refined by column chromatography filled with neutral alumina (developing solvent, diethyl ether: chloroform=1:1 (vol. ratio)). However, it was found that tetrabutylammonium tetracyanoborate was not at all produced and tetrabutylammonium bromide, a starting material, remained.

Further, the above-mentioned precipitate and the refined product were analyzed by $^{11}$B—NMR to find no peak derived from tetracyanoborate.

The same reaction was tried by changing the reaction container to a sealed pressure resistant container (capacity: 100 ml, inner cylinder of Teflon (registered trade name), made of stainless steel), however, no product was obtained.

The respective various physical properties of the ionic compounds obtained by the respective Synthesis Examples were measured by the above-mentioned measurement methods and the results are shown in Table 1.

TABLE 1

| | Compound (part by mass) | γ-Butyrolactone (part by mass) | Ion conductivity (S/cm) (25° C.) | Thermal decomposition starting temperature (° C.) | Potential window (V) |
|---|---|---|---|---|---|
| Synthesis Example 1-1 | Bu$_4$NTCB 35 | 65 | 0.009 | 210 | −3.2~+2.0 |
| Synthesis Example 1-2 | EMImTCB 35 | 65 | 0.021 | 330 | −2.4~+2.0 |
| Synthesis Example 1-3 | Et$_3$HNTCB 35 | 65 | 0.018 | 285 | −1.7~+2.0 |
| Synthesis Example 1-4 | Et$_3$MeNTCB 35 | 65 | 0.018 | 280 | −3.0~+2.0 |
| Synthesis Example 1-5 | Et$_4$NTCB 35 | 65 | 0.015 | 220 | −3.0~+2.0 |

From the above-mentioned results, according to the first production method of the invention, reaction was promoted at a lower temperature (130° C. to 150° C.) than that in the case of using an alkali metal cyanide (reaction temperature: 250° C.). Further, without using costly trimethylsilyl cyanide, a tetracyanoborate-containing ionic compound could bewas obtained stably.

Experiment Examples 1 to 2 and Comparative Experiment Examples 1 to 4

The thermal decomposition starting temperature was measured for mixtures containing 1-ethyl-3-methylimidazolium tetracyanoborate synthesized in Synthesis Example 1-2 and mixtures containing 1-ethyl-3-methylimidazolium tetrafluoroborate (EtMeImBF$_4$), as an impurity (for organic synthesis, made available by Wako Pure Chemical Industries, Ltd.), in the mixing ratio compositions shown in the following Table 2. The measurement was carried out by the following measurement 2 of thermal decomposition starting temperature. The results are shown in Table 2.

[Measurement of Thermal Decomposition Starting Temperature 2]

In an aluminum pan, 5 mg of each ionic compound having a composition shown in the following Table 2 was put and elevated temperature at 10° C./min to 230° C. and at 0.5° C./min from 230° C. to 350° C. and the temperature when the weight was decreased by 2% from the initial weight was measured with a thermo gravimetry differential thermal analyzer ("EXSTAR 6000 TG/DTA", manufactured by Seiko Instrument Inc.).

TABLE 2

| | EMeIm B(CN)$_4$ (mol %) | EMeIm BF$_4$ (mol %) | Thermal decomposition starting temperature (° C.) |
|---|---|---|---|
| Experiment Example 1 | 100 | 0 | 304 |
| Experiment Example 2 | 97 | 3 | 289 |
| Comparative Experiment Example 1 | 95 | 5 | 276 |
| Comparative Experiment Example 2 | 90 | 10 | 265 |
| Comparative Experiment Example 3 | 75 | 25 | 262 |
| Comparative Experiment Example 4 | 50 | 50 | 261 |

From Table 2, it can be understood that as the content of fluorine atom-containing impurities was increased, the thermal decomposition starting temperature was deceased and in the case fluorine atom-containing impurities were contained in the ionic compound, the physical property (heat resistance) of the ionic compound was deteriorated.

Further, it can be understood that the thermal decomposition starting temperature of Comparative Experimental Example 1 was lower by no less than 20° C. as compared with that of Experimental Example 1 and when the content of F atom-containing impurities exceeds 5 mol %, the material durability under high temperature condition was considerably deteriorated. It is supposedly attributed to that the impurities having B—F bond and contained in the ionic compound were reacted with oxygen atoms of water and oxygen existing in air and decomposed.

In Experimental Examples 1 and 2 having the content of F atom-containing impurities of 3 mol % or lower, decrease of the thermal decomposition starting temperature was little. Further, from the results of Table 1, it can be understood the product is preferably usable as an electrolytic solution material.

Experimental Example 3

A resin composition was obtained by adding 10 parts by weight of 1-ethyl-3-methylimidazolium tetracyanoborate as a conductivity supplying agent to 90 parts by weight of hydrogen-terminated ethylene oxide/propylene oxide copolymer and heating and kneading the mixture at 70° C.

Next, 20 parts by weight of the obtained resin composition was added to 100 parts by weight of a methyl methacrylate polymer (molecular weight; about 200,000), which is a thermoplastic resin, and the mixture was heated and kneaded at 100° C. by a test roll apparatus ("HR-2 model", manufactured by Nisshin Kagaku Inc.) to obtain a sheet having an even thickness of 2 mm.

When the surface resistance of the obtained sheet was measured by a surface resistance measurement device ("HT-210", manufactured by Mitsubishi Chemical Corporation), it was $9 \times 10^7 \Omega$. No ionic compound bleeding was observed.

From the results of Experimental Example 3, it is found that the ionic compound of the invention could be used preferably as a conductivity supplying agent.

Experimental Example 4

The flow point, dynamic viscosity, and friction coefficient of 1-ethyl-3-methylimidazolium tetracyanoborate synthesized in Synthesis Example 1-2 were evaluated.

The flow point was evaluated according to JIS K2269-1987. The observed flow point of EtMeImTCB was −20° C. The dynamic viscosity was evaluated according to JIS K2283-2000. The dynamic viscosity of EtMeImTCB at 40° C. was 30 cSt ($3.0 \times 10^{-5}$ m$^2$/s). The friction coefficient was measured by a pendulum-type friction tester ("Soda pendulum-type oiliness friction tester" manufactured by Shinko Engineering Co., Ltd.). The friction coefficient of EtMeImTCB was 0.16.

From the results of Experimental Example 4, it can be understood that the ionic compound of the invention had fluidity even in low temperature environments and also a low friction coefficient and thus was suitable as a lubricant.

Since the content of F atoms and impurities containing F atom was lowered to an extremely low level in the ionic compound of the invention, in the case of being used for various kinds of applications, the ionic compound exerts stable characteristics (thermal, physical, and electrochemical characteristics) without causing a problem such as corrosion of peripheral members.

Example 2

In Synthesis Example 2, an ionic compound having tetracyanoborate as an anion was synthesized by using an ammonium cyanide compound as a starting material.

Raw Material Synthesis: Ammonium Cyanide Synthesis 1

To a 2 L flask equipped with a stirring device, and a dripping funnel, 200 ml of methylene chloride and 67.6 g (200 mmol) of tetrabutylammonium sulfoxide were added and stirred, then, 50 ml of an aqueous 4 M NaOH solution was added to the resulting solution and stirred. After 10 g (204 mmol) of sodium cyanide previously dissolved in 20 ml of water was dropwise added through a dripping funnel to the obtained methylene chloride solution, the mixed solution was stirred for 30 minutes at room temperature (25° C.). The obtained suspension was filtered and the filtrate was concentrated to obtain 58.7 g of oily crude tetrabutylammonium cyanide.

Synthesis Example 2-1

Tetrabutylammonium Tetracyanoborate (Bu$_4$NTCB) Synthesis 1

After a 50 ml flask equipped with a stirring device, a dripping funnel, and a reflux condenser was purged with nitrogen, and under nitrogen atmosphere at room temperature 0.64 g (2.0 mmol) of tetrabutylammonium bromide, 2.65 g (9.9 mmol) of tetrabutylammonium cyanide, 0.35 g (1.4 mmol) of boron tribromide, and 1.4 ml of toluene were added, the contents were stirred for 2 days while being heated in an oil bath at 130° C. After 2 days, toluene was removed from the flask in reduced pressure to obtain a black solid.

The black solid was put in a beaker equipped with a stirring device, 100 ml of chloroform and 100 ml of water were added thereto, the chloroform layer was extracted by a separatory funnel and the chloroform layer was washed separately with 100 ml of water twice, and thereafter, the chloroform layer was concentrated in reduced pressure to obtain an oily crude product. The crude product was refined by column chromatography filled with neutral alumina (developing solvent, a mixed solution of diethyl ether and chloroform) and a fraction containing the product was separately obtained and dried by removing the solvent to obtain tetrabutylammonium tetracyanoborate, as a product (yellow solid, produced amount: 0.39 g (1.4 mmol), yield: 77%, melting point: 90° C.).

The respective various physical properties of the obtained tetrabutylammonium tetracyanoborate, which is an ionic compound, were measured by the above-mentioned measurement methods and the results are shown as follows. The product showed an NMR spectrum same as that of the product of Synthesis Example 1-1.

Ion conductivity (25° C.): 0.009 S/cm
Thermal decomposition starting temperature: 210° C.
Potential Window: −3.2 V to 2.0 V
$^1$H-NMR (d6-DMSO): δ3.16 (m, 8H), 1.56 (m, 8H), 1.30 (ddq, J=11 Hz, J=11 Hz, J=7.2 Hz, 8H), 0.92 (t, J=7.2 Hz, 12H)
$^{13}$C-NMR (d6-DMSO): 8121.9 (m), 57.7 (s), 39.1 (s), 19.4 (s), 13.7 (s)
$^{11}$B—NMR (d6-DMSO): δ−39.6 (s)

Synthesis Example 2-2

Tetrabutylammonium Tetracyanoborate Synthesis 2

The same operation as that of Synthesis Example 2-1 was carried out, except that 1.4 ml (1.4 mmol, 1 M-p-xylene solution, manufactured by Aldrich) of boron trichloride was used in place of boron tribromide and no toluene was used to obtain tetrabutylammonium tetracyanoborate, as a product (yellow solid, produced amount: 0.21 g (0.6 mmol), yield: 42%, melting point: 90° C.).

The product showed an NMR spectrum and various physical properties similar to those of the product of Synthesis Example 2-1.

Synthesis Example 2-3

Tetrabutylammonium Tetracyanoborate Synthesis 3

The same operation as that of Synthesis Example 2-2 was carried out, except that no tetrabutylammonium bromide was used to obtain tetrabutylammonium tetracyanoborate, as a product (yellow solid, produced amount: 0.18 g (0.5 mmol), yield: 35%, melting point: 90° C.).

The product showed an NMR spectrum and various physical properties similar to those of the product of Synthesis Example 2-1.

Synthesis Example 2-4

Tetrabutylammonium tetracyanoborate (Bu$_4$NTCB) synthesis 4

After a 50 ml flask equipped with a stirring device, a dripping funnel, and a reflux condenser was purged with nitrogen, and under nitrogen atmosphere at room temperature 0.64 mg (2.0 mmol) of tetrabutylammonium bromide, 1.65 g (6.2 mmol) of tetrabutylammonium cyanide, 0.20 g (1.4 mmol) of triethyl borate, and 1.4 ml of dimethylsulfoxide were added, the contents were stirred for 2 days while being heated in an oil bath at 170° C. After 2 days, the organic solvent was removed from the flask in reduced pressure to obtain a black solid.

The black solid was put in a beaker equipped with a stirring device, 100 ml of chloroform and 100 ml of water were added thereto, the chloroform layer was extracted by a separatory funnel and the chloroform layer was washed separately with 100 ml of water twice, and thereafter, the chloroform layer was concentrated in reduced pressure to obtain an oily crude product. The crude product was refined by column chromatography filled with neutral alumina (developing solvent: a mixed solution of diethyl ether and chloroform) and a fraction containing the product was separately obtained and dried by removing the solvent to obtain tetrabutylammonium tetracyanoborate, as a product (yellow solid, produced amount: 0.1 g (0.3 mmol), yield: 20%, melting point: 90° C.).

The product showed an NMR spectrum and various physical properties similar to those of the product of Synthesis Example 2-1.

Synthesis Example 2-5

Tetrabutylammonium Tetracyanoborate Synthesis 5

After a 2 L flask equipped with a stirring device, a dripping funnel, and a reflux condenser was loaded with 58.7 g of un-refined tetrabutylammonium cyanide obtained by raw material synthesis and 11.6 g (36.3 mmol) of tetrabutylammonium bromide and purged with nitrogen, 26 ml (26 mmol) of a p-xylene solution of 1 M boron trichloride was dropwise added to the flask through a dripping funnel at room temperature. While being heated at 150° C., the reaction solution was stirred for 2 days and thereafter, the solvent was removed and the obtained residue was refined by column chromatography using neutral alumina as a packing material (developing solvent: a mixed solvent obtained by mixing dichloroethane and diethyl ether at 1:1 (vol. ratio)) to obtain tetrabutylammonium tetracyanoborate (produced amount: 3.2 g (9 mmol), yield: 35%).

The product showed an NMR spectrum and various physical properties similar to those of the product of Synthesis Example 2-1.

Synthesis Example 2-6

Tetrabutylammonium Tetracyanoborate Synthesis 6

After a 50 ml flask equipped with a stirring device, a dripping funnel, and a reflux condenser was purged with nitrogen, and under nitrogen atmosphere and at room temperature, 0.65 g (2.0 mmol) of tetrabutylammonium bromide, 2.98 g (11.0 mmol) of tetrabutylammonium cyanide, and 2.0 ml (2.0 mmol) of a p-xylene solution of 1 M boron trichloride were added, the contents were stirred for 2 days while being heated in an oil bath at 150° C. Thereafter, the solvent was removed to obtain a black solid.

The obtained crude product was made to be an ethyl acetate solution of 10 wt % and mixed with 2.1 g of activated carbon (Carborafin (registered trade name)-6 manufactured by Japan EnviroChemicals, Ltd.) and stirred for 30 minutes at room temperature. Thereafter, the obtained activated carbon suspension was filtered with a membrane filter (0.2 μm, made of PTFE, hydrophilic), operation involving dispersing activated carbon on the filter in 6.5 g of ethyl acetate, stirring the obtained dispersion at 50° C. for 10 minutes and filtering the dispersion again was repeated 5 times. Obtained filtrate and washing solution were mixed and dried by removing the solvent to obtain brown solid.

Next, the obtained brown solid was mixed with 0.7 g of hydrogen peroxide (aqueous 30 wt % solution) and stirred for 60 minutes at 50° C. After 3 g of butyl acetate was added to the obtained solution and stirred for 30 minutes at room temperature to produce dispersion state, the dispersion was transferred to a container for centrifugal separation and then the container was shaken for 90 seconds and subjected to centrifugal separation (1700 rpm, 10 minutes). Thereafter, the upper layer (butyl acetate layer) was concentrated and obtained light yellow solid was coarsely dried for 30 minutes at 80° C. in reduced pressure and the crude product was pulverized with a mortar to obtain a powder. The powder was spread on a tray and further dried for 3 days at 80° C. in reduced pressure to obtain tetrabutylammonium tetracyanoborate, a desired product, (produced amount 0.36 g (1.0 mmol), yield 50%).

The product showed an NMR spectrum and various physical properties similar to those of the product of Synthesis Example 2-1.

Synthesis Example 2-7

Triethylmethylammonium Tetracyanoborate Synthesis

The same operation as that of Synthesis Example 2-6 was carried out, except that 1.5.6 g (11 mmol) of triethylmethylammonium cyanide was used in place of tetrabuthylammonium cyanide and no tetrabuthylammonium bromide was used to obtain triethylmethylammonium tetracyanoborate ($Et_3MeNTCB$), as a product (light yellow solid, produced amount: 0.23 g (1 mmol), yield: 50%, melting point: 115° C.). The product showed an NMR spectrum and various physical properties similar to those of the product of Synthesis Example 1-4.

According to the second production method of the invention, the ionic compound having tetracyanoborate can be produced in reaction temperature condition of 200° C. or lower. Further, without using costly trimethylsilane cyanide, the ionic compound having tetracyanoborate is obtained.

Example 3

In Example 3, an ionic compound having tetracyanoborate was synthesized by using an trimethylsilyl cyanide as a starting material.

Synthesis Example 3-1

Triethylmethylammonium Tetracyanoborate ($Et_3MeNTCB$) Synthesis 1

To a 1 L eggplant flask equipped with a stirring device, a reflux condenser, a discharge device, and dripping funnel, 30.3 g (200 mmol) of previously heated and dried triethylmethylammonium chloride ($Et_3MeNCl$) was added. After the container was purged with nitrogen, 109.0 g (1100 mm) of trimethylsilyl cyanide (TMSCN) was added at room temperature and stirred and mixed. Next, 200 mL (200 mmol) of a p-xylene solution of 1 mol/L boron trichloride was gradually and dropwise added through the dripping funnel. On completion of the dropwise addition, the reaction container was heated to 150° C. and reaction was carried out while trimethylsilyl chloride (TMSCl, boiling point: about 57° C.) generated as a byproduct being discharged through a reflux discharge part.

After 30 hour heating and stirring, the inside pressure of the reaction container was reduced by a diaphragm pump and a p-xylene solution of TMSCN was removed through the reflux discharge part. Thereafter, 45 g of the crude product and 225 g of ethyl acetate were put in a 500 mL beaker equipped with a stirring device and stirred for 5 minutes for dissolution and 135 g of activated carbon (Carborafin (registered trade name)-6 manufactured by Japan EnviroChemicals, Ltd.) was added thereto and stirred for 10 minutes. The obtained activated carbon suspension was filtered with a membrane filter (0.2 μm, made of PTFE) and the solvent was removed and obtained product was dried to obtain triethylmethylammonium tetracyanoborate, an desired product, (light yellow solid) (produced amount: 37.9 g (164 mmol), yield: 82%, melting point: 115° C.).

The various physical properties of the obtained triethylmethylammonium tetracyanoborate were measured by the above-mentioned measurement methods. The results are as follows.

Ion conductivity (25° C.): 0.018 S/cm
Thermal decomposition starting temperature: 280° C.
Potential window: −3.2 V to 2.0 V
$^1$H-NMR(d6-DMSO) δ 3.23(q,J=6.8 Hz,6H), 2.86(s,3H), 1.18(t,J=6.8 Hz,9H)
$^{13}$C-NMR(d6-DMSO) δ 112.5(m), 55.2(s), 46.2(s), 7.7(s)
$^{11}$B—NMR(d6-DMSO) δ −39.6(s)

Synthesis Example 3-2

Triethylmethylammonium Tetracyanoborate Synthesis 2

Triethylmethylammonium tetracyanoborate (liquid yellow solid) was obtained in the same manner as that in Synthesis Example 3-1, except that refining was carried out by column chromatography in place of activated carbon filtration (produced amount: 37.9 g (164 mmol), yield: 82%, melting point: 115° C.).

The refining method was as follows: 45 g of the crude product and 20 mL of a mixed solution of methylene chloride and acetonitrile (4:1 (vol. ratio)) were added to a 500 mL beaker and stirred for 5 minutes for dissolution. Next, refining was carried out by column chromatography using aluminum oxide (450 cc) as a fixed phase and a mixed solvent of methylene chloride and acetonitrile (4:1 (vol. ratio), 2.5 L) as a moving phase to obtain triethylmethylammonium tetracyanoborate, an desired product. The product showed an NMR spectrum and various physical properties same as those of the product of Synthesis Example 3-1.

Synthesis Example 3-3

Tetrabutylammonium Tetracyanoborate (Bu$_4$NTCB) Synthesis

Tetrabutylammonium tetracyanoborate (white solid) as a desired product was obtained in the same manner as that in Synthesis Example 3-1, except that 64.5 g (200 mmol) of tetrabutylammonium bromide was employed in place of Et$_3$MeNCl employed in Synthesis Example 3-1 (produced amount: 60.0 g (196 mmol), yield: 98%, melting point: 90° C.). The product showed an NMR spectrum and various physical properties similar to those of the product of Synthesis Example 1-1.

Ion conductivity (25° C.): 0.009 S/cm
Thermal decomposition starting temperature: 210° C.
Potential window: −3.2 V to 2.0 V Synthesis Example 3-4

1-ethyl-3-Methylimidazolium Tetracyanoborate (EtMeImTCB) Synthesis

As a desired product, 1-ethyl-3-methylimidazolium tetracyanoborate (light yellow liquid) was obtained in the same manner as that in Synthesis Example 3-1, except that 38.2 g (200 mmol) of 1-ethyl-3-methylimidazolium bromide was employed in place of Et$_3$MeNCl (produced amount: 24.9 g (110 mmol), yield: 55%, melting point: 15° C.). The product showed an NMR spectrum and various physical properties similar to those of the product of Synthesis Example 1-2.

Ion conductivity (25° C.): 0.021 S/cm
Thermal decomposition starting temperature: 330° C.
Potential window: −2.4 V to 2.0 V Synthesis Example 3-5

Triethylammonium Tetracyanoborate (Et$_3$NHTCB) Synthesis 1

Triethylammonium tetracyanoborate (light yellow liquid), as a desired product, was obtained in the same manner as that in Synthesis Example 3-1, except that 20.2 g (200 mmol) of triethylamine was employed in place of Et$_3$MeNCl (produced amount: 23.8 g (110 mmol), yield: 60%, melting point: 150° C.). The product showed an NMR spectrum and various physical properties similar to those of the product of Synthesis Example 1-3.

Ion conductivity (25° C.): 0.018 S/cm
Thermal decomposition starting temperature: 285° C.
Potential window: −1.7 V to 2.0 V Synthesis Example 3-6

Triethylammonium Tetracyanoborate (Et$_3$NHTCB) Synthesis 2

Triethylammonium tetracyanoborate (light yellow liquid), as a product, was obtained in the same manner as that in Synthesis Example 3-1, except that 27.5 g (200 mmol) of triethylammonium chloride was employed in place of Et$_3$MeNCl (produced amount: 23.8 g (110 mmol), yield: 60%, melting point: 150° C.). The product showed an NMR spectrum and various physical properties similar to those of the product of Synthesis Example 3-5.

Synthesis Example 3-7

Tetraethylammonium Tetracyanoborate (Et$_4$NTCB) Synthesis 1

Tetraethylammonium tetracyanoborate (white solid), as a product, was obtained in the same manner as that in Synthesis Example 3-1, except that 33.1 g (200 mmol) of tetraethylammonium chloride was employed in place of Et$_3$MeNCl (produced amount: 46.6 g (190 mmol), yield: 95%, melting point: 150° C.). The product showed an NMR spectrum and various physical properties similar to those of the product of Synthesis Example 1-5.

Ion conductivity (25° C.): 0.015 S/cm
Thermal decomposition starting temperature: 220° C.
Potential window: −3.0 V to 2.0 V Synthesis Example 3-8

Triethylmethylammonium Tetracyanoborate Synthesis 3

The same operation as that of Synthesis Example 3-1 was carried out, except that a 1 L pressure-resistant container (made of stainless steel, usable in pressurized condition at 5 kPa) was used in place of the eggplant flask and TMSCl generated as a byproduct during the reaction was not extracted to obtain light yellow solid triethylmethylammonium tetracyanoborate (produced amount: 33.3 g (144 mmol), yield: 72%, melting point: 115° C.) as a product. The obtained product showed an NMR spectrum and various physical properties similar to those of the product of Synthesis Example 3-1.

Synthesis Example 3-9

Tetrabutylammonium Tetracyanoborate (Bu$_4$NTCB) Synthesis 2

Tetrabutylammonium tetracyanoborate (white solid), as a product, was obtained in the same manner as that in Synthesis Example 3-3, except that 20.8 g (200 mmol) of trimethyl borate was employed in place of boron trichloride and the reaction container was heated to 170° C. (produced amount: 50.0 g (140 mmol), yield: 70%, melting point: 90° C.). The product showed an NMR spectrum and various physical properties similar to those of the product of Synthesis Example 3-3.

Synthesis Example 3-10

Tetrabutylammonium Tetracyanoborate (Bu$_4$NTCB) Synthesis 3

Tetrabutylammonium tetracyanoborate (white solid), as a product, was obtained in the same manner as that in Synthesis Example 3-3, except that 29.2 g (200 mmol) of triethyl borate was employed in place of boron trichloride and the reaction container was heated to 170° C. (produced amount: 50.0 g (140 mmol), yield: 70%, melting point: 90° C.). The product showed an NMR spectrum and various physical properties similar to those of the product of Synthesis Example 3-3.

Synthesis Example 3-11

Tetrabutylammonium Tetracyanoborate (Bu$_4$NTCB) Synthesis 4

Tetrabutylammonium tetracyanoborate (white solid), as a product, was obtained in the same manner as that in Synthesis Example 3-3, except that 28.4 g (200 mmol) of boron trifluoride diethyl ether complex was employed in place of boron trichloride and the reaction container was heated to 170° C. (produced amount: 53.6 g (150 mmol), yield: 75%, melting point: 90° C.). The product showed an NMR spectrum and various physical properties similar to those of the product of Synthesis Example 3-3.

Synthesis Example 3-12

Triethylmethylammonium Tetracyanoborate Synthesis 4

Triethylmethylammonium tetracyanoborate (light yellow solid), as a product, was obtained in the same manner as that in Synthesis Example 3-1, except that butyl acetate was employed in place of p-xylene (produced amount: 27.7 g (120 mmol), yield: 55%, melting point: 115° C.). The product showed an NMR spectrum and various physical properties similar to those of the product of Synthesis Example 3-1.

Synthesis Example 3-13

Triethylmethylammonium Tetracyanoborate Synthesis 5

Reaction same as Synthesis Example 3-1 was carried out and 69.5 g (640 mmol) of TMSCl discharged out through the reflux discharge part was added to a flask (capacity 500 mL) equipped with a stirring device and then 64.7 g (640 mmol) of triethylamine and 17.3 g (640 mmol) of hydrogen cyanide were added at room temperature (25° C.) and stirred overnight. The obtained product was distilled to obtain TMSCN (colorless liquid, produced amount: 57.1 g (576 mmol), yield: 90%).

Triethylmethylammonium tetracyanoborate was obtained in the same manner as that in Synthesis Example 3-1, except that 52.1 g (525 mmol) of TMSCN obtained by using TMSCl, a reaction byproduct, as a raw material and 12.3 g (105 mmol) of BCl$_3$ and 15.9 g (105 mmol) of TEMACl were used (produced amount: 19.8 g (86 mmol), yield: 82%, melting point: 115° C.). The obtained product showed an NMR spectrum and various physical properties similar to those of the product of Synthesis Example 3-1.

Synthesis Example 3-14

Tetramethylammonium Tetracyanoborate Synthesis

Tetramethylammonium tetracyanoborate (white solid), as a product, was obtained in the same manner as that in Synthesis Example 3-1, except that 21.9 g (200 mmol) of tetramethylammonium chloride was employed in place of Et$_3$MeNCl (produced amount: 26.5 g (140 mmol), yield: 70%,).
$^1$H-NMR(d6-DMSO) δ 3.08(s, 12H)
$^{13}$C-NMR(d6-DMSO) δ 121.9(m), 55.3(s)
$^{11}$B—NMR(d6-DMSO) δ −39.6(s)

Synthesis Example 3-15

Ammonium Tetracyanoborate Synthesis

Ammonium tetracyanoborate (white solid), as a product, was obtained in the same manner as that in Synthesis Example 3-1, except that 10.7 g (200 mmol) of ammonium chloride was employed in place of Et$_3$MeNCl (produced amount: 8.0 g (60 mmol), yield: 30%,).
$^1$H-NMR(d6-DMSO) δ 6~7(broad,4H)
$^{13}$C-NMR(d6-DMSO) δ 121.9(m)
$^{11}$B—NMR(d6-DMSO) δ −39.6(s)

Synthesis Example 3-16

Tributylammonium Tetracyanoborate Synthesis

Tributylammonium tetracyanoborate (yellow solid), as a product, was obtained in the same manner as that in Synthesis Example 3-1, except that 44.4 g (200 mmol) of tributylammonium chloride was employed in place of Et$_3$MeNCl (produced amount: 48.2 g (160 mmol), yield: 80%).
$^1$H-NMR(d6-DMSO) δ 2.98(m,6H), 1.4~1.8(m,6H), 1.2~1.3 (m,6H), 0.94(m,9H)
$^{13}$C-NMR(d6-DMSO) δ 121.9(m), 52.7(s), 26.2(s), 20.3(s), 14.4(s)
$^{11}$B—NMR(d6-DMSO) δ −39.6(s)

Synthesis Example 3-17

Lithium Tetracyanoborate Synthesis

A beaker having a capacity of 500 mL and equipped with a stirring device was loaded with 48.2 g (160 mmol) of tributylammonium tetracyanoborate obtained by Synthesis Example 3-16, 200 g of butyl acetate, 4.6 g (192 mmol) of lithium hydroxide monohydrate, and 200 g of ultrapure water and the contents were stirred for 1 hour. Thereafter, the mixed solution was transferred to a separatory funnel and kept still and the mixed solution was separated into two layers. Between the layers, the lower layer (water layer) was separated and concentrated to give a light yellow solid, the obtained light yellow solid was mixed with 200 g of acetonitrile and stirred. Successively, the obtained solution was filtered with a membrane filter (0.2 μm, made of PTFE) and solvent was evaporated to obtain lithium tetracyanoborate (white solid), a desired product (produced amount: 13.6 g (112 mmol), yield: 70%).
$^7$Li-NMR(d6-DMSO)δ 0.02(s)
$^{13}$C-NMR(d6-DMSO)δ 121.9(m)
$^{11}$B—NMR(d6-DMSO)δ −39.6(s)

Synthesis Example 3-18

Triethylmethylammonium Tetracyanoborate Synthesis 6

The same reaction as that in Synthesis Example 3-1 was carried out, and 69.5 g (640 mmol) of TMSCl extracted through the reflux discharge part was added to a flask (capacity 500 mL) equipped with a stirring device and next, 103.2 g (640 mmol) of hexamethyldisilazane and 51.9 g (1919 mmol) of hydrogen cyanide were added and the mixture was stirred overnight. The obtained product was distilled to obtain TMSCN (colorless liquid, produced amount: 171.4 g (1727 mmol), yield: 90%).

Triethylmethylammonium tetracyanoborate was obtained in the same manner as that in Synthesis Example 3-1, except that 52.1 g (525 mmol) of TMSCN obtained by using TMSCl, a reaction byproduct, as a raw material and 12.3 g (105 mmol) of boron trichloride, and 15.9 g (105 mmol) of Et$_3$MeNCl were used (light yellow solid, produced amount: 19.8 g (86 mmol), yield: 82%, melting point: 115° C.). The obtained product showed an NMR spectrum and various physical properties similar to those of the product of Synthesis Example 3-1.

Synthesis Example 3-19

Trimethylsilylammonium Tetracyanoborate (Me$_3$SiTCB) Synthesis 1

Trimethylsilylammonium tetracyanoborate, as a product, was obtained in the same manner as that in Synthesis Example 3-1, except that no Et$_3$MeNCl was employed. Produced amount was 1.9 g (10 mmol), and yield was 90%.

Synthesis Example 3-20

Triethylmethylammonium Tetracyanoborate Synthesis 7

The same operation as that of Synthesis Example 3-1 was carried out, except that 71.6 g (1100 mmol) of potassium cyanide was used in place of trimethylsilyl cyanide, however triethylmethylammonium tetracyanoborate, an desired product, was not at all obtained.

In the third production method of the invention, since the activity deterioration of reaction by a reaction byproduct is hardly caused, an ionic compound containing tetracyanoborate ion can be produced at a higher yield as compared that by a conventional method. Further, in the case an ammonium salt is used, an ionic compound containing an organic cation can be produced in one step.

Synthesis Example 3-21

Tributylammonium Tetracyanoborate Synthesis 2

The same operation as that of Synthesis Example 3-16 was carried out except that 42.5 g (200 mmol) of tributylammonium cyanide in place of tetrabutylammonium chloride, and 84.8 g (855 mmol) of trimethylsilyl cyanide were used to obtain yellow solid tributylammonium tetracyanoborate as a product (produced amount: 42.5 g (141 mmol), yield: 75%). The obtained product showed an NMR spectrum and various physical properties similar to those of the product of Synthesis Example 3-16.

Example 4

In Example 4, an ionic compound having tetracyanoborate as an anion was synthesized by using hydrogen cyanide (HCN) as a starting material.

Synthesis Example 4-1

Tributylammonium Tetracyanoborate Synthesis

A 200 ml three-neck flask equipped with a heating device, a stirring device and a reflux condenser was purged with nitrogen and 10.2 g (55 mmol) of tributylamine and 1.49 g (55 mmol) of hydrogen cyanide were added at room temperature and stirred for 1 hour. Successively, 1.17 g (10 mmol) of boron trichloride and 100 ml of p-xylene were further added and the contents were heated and refluxed for 2 days at 150° C. After 30 g of butyl acetate was added to the obtained solution and stirred at room temperature, 9 g of activated carbon (Carborafin (registered trade name)-6 manufactured by Japan EnviroChemicals, Ltd.) was added thereto and stirred for 20 minutes at room temperature. The obtained activated carbon suspension was filtered with a membrane filter (0.5 μm, made of PTFE) and operation involving washing activated carbon on the filter with 30 g of butyl acetate was repeated 5 times. Obtained filtrate and washing solution were mixed and dried by removing the solvent to obtain black solid.

Next, the obtained black solid was mixed with 8 g of hydrogen peroxide water and stirred for 1 hour at 50° C., thereafter, 40 g of butyl acetate was added to the obtained solution and stirred further for 20 minutes at room temperature and the solution was kept still for 10 minutes and successively, the butyl acetate layer was separated, removed the solvent therefrom and dried to obtain an oily brown tributylammonium tetracyanoborate (Bu$_3$NHTCB) (produced amount 1.21 g (4 mmol), yield 40%).
$^1$H-NMR(d6-DMSO)δ 8.8 (br, 1H), 2.99 (dd,J=8.0 Hz,J=16.4 Hz,6H), 1.52 (m,6H), 1.28 (m,6H), 0.88 (m,9H)
$^{13}$C-NMR(d6-DMSO)δ 121.9 (m), 46.0 (s), 8.8 (s)
$^{11}$B—NMR(d6-DMSO)δ −39.6 (s)

Synthesis Example 4-2

Triethylammonium Tetracyanoborate Synthesis

Triethylammonium tetracyanoborate was obtained in the same manner as that in Synthesis Example 4-1, except that 5.58 g (55 mmol) of triethylamine was employed in place of tributylamine (brown solid, produced amount: 0.65 g (3 mmol), yield: 30%). The NMR data of the obtained triethylammonium tetracyanoborate is indicated below. The various physical properties measured by the above-mentioned measurement methods are as follows.

Ion conductivity (25° C.): 0.018 S/cm
Thermal decomposition starting temperature: 285° C.
Potential window: −1.7 V to 2.0 V
$^1$H-NMR(d6-DMSO) δ 8.83 (s,1H), 3.10 (q,J=7.2 Hz,6H), 1.17 (t,J=7.2 Hz,9H)
$^{13}$C-NMR(d6-DMSO) δ 121.9 (m), 46.0 (s), 8.8 (s)
$^{11}$B—NMR(d6-DMSO) δ −39.6 (s)

According to the invention, an ionic compound containing tetracyanoborate can be obtained by using economical hydrogen cyanide as a starting material.

According to the fourth production method of the invention, since hydrogen cyanide is used as a cyanide source, an ionic compound containing tetracyanoborate can be obtained economically as compared with a conventional method.

Example 5

In Example 5, the amount of impurities contained in each ionic compound obtained by the following Synthesis Examples 5 to 11 was measured. Measurement methods of the respective type impurities are as follows.

[Measurement of Metal Component Content]
(1) Measurement by ICP (Measurement of Na and Si)

Each 2 g of respective ionic compounds obtained by the following Synthesis Examples 5 to 11 were diluted with ultrapure water (higher than 18.2 Ω·cm) 10 to 100 times as much to obtain measurement solutions, and amounts of Na and Si contained in each ionic compound were measured by using an ICP emission spectrophotometer ICPE-9000 (manufactured by Shimadzu Corporation).

(2) Measurement by Ion Chromatography (Measurement of Halide Ions)

Each 0.3 g of respective ionic compounds obtained by the following Synthesis Examples were diluted with ultrapure water (higher than 18.2 Ω·cm) 100 to 1000 times as much to obtain measurement solutions, and the amount of halide ions contained in each ionic compound was measured by using ion chromatography system ICS-3000 (manufactured by Nippon Dionex K.K.).

Separation mode: ion exchange
Detector: Electric conductivity detector CD-20
Column: Anion analysis column AS 17-C (manufactured by Nippon Dionex K.K.).

(3) Measurement by Ion Chromatography (Measurement of CN$^-$)

Each 0.1 g of respective ionic compounds obtained by the following Synthesis Examples were diluted with ultrapure water (higher than 18.2 Ω·cm) 10000 times as much to obtain measurement solutions, and the amount of cyanide ion (CN$^-$) contained in each ionic compound was measured by using ion chromatography system ICS-1500 (manufactured by Japan Dionex Co., Ltd.).

Separation mode: ion exchange
Eluent: 10 mmol aqueous H$_2$SO$_4$ solution
Regeneration solution: 0.5 mmol aqueous NaOH solution
Detector: Electrochemical detector ED-50A
Column: Anion analysis column ICE-AS1

[Water Measurement]

The amount of water in each sample was measured by using water measurement apparatus "AQ-2000" manufactured by Hiranuma Sangyo Co., Ltd. The sample injection amount was 0.1 ml and "Hydranal Aqualite RS-A" (commercialized by Hiranuma Sangyo Co., Ltd.) was used as an anolyte and "Aqualite CN" was used as a catholyte (manufactured by Kanto Chemical Co., Inc.). Each sample was injected through a sample injection inlet by using an injection syringe for avoiding contact with atmospheric air.

Hereinafter, in Synthesis Example 5, ionic compound synthesis was carried out by using starting materials containing trimethylsilyl cyanide.

Synthesis Example 5

Synthesis Example 5-1

Triethylmethylammonium Tetracyanoborate Synthesis

<Synthesis of Crude Production>

A 1 L eggplant flask equipped with a stirring device, a reflux condenser, a discharge device, and dripping funnel was loaded with 30.3 g (200 mmol) of previously heated and dried triethylmethylammonium chloride (Et$_3$MeNCl). After the container was purged with nitrogen, 109.0 g (1100 mm) of trimethylsilyl cyanide (TMSCN) was added at room temperature and stirred and mixed. Next, 200 mL (200 mmol) of a p-xylene solution of 1 mol/L boron trichloride (BCl$_3$) was gradually and dropwise added through the dripping funnel. On completion of the dropwise addition, the reaction container was heated to 150° C. and reaction was carried out while trimethylsilyl chloride (TMSCl, boiling point: about 57° C.) generated as a byproduct being discharged through a reflux discharge part.

After 30 hour heating and stirring, the inside pressure of the reaction container was reduced by a diaphragm pump and a p-xylene solution of TMSCN was removed through the reflux discharge part. In the container, crude triethylmethylammonium tetracyanoborate (Et$_3$MeNTCB) was produced.

<Activated Carbon Treatment>

Next, 46.0 g of the obtained crude product was dissolved in ethyl acetate in a 500 mL beaker equipped with a stirring device to obtain a 10 wt % ethyl acetate solution, and 65 g of activated carbon (Carborafin (registered trade name) manufactured by Japan EnviroChemicals, Ltd.) was added thereto and heated by a water bath until the inner temperature became 50° C. Successively, after being stirred for 10 minutes at 50° C., the obtained activated carbon suspension was filtered with a membrane filter (0.2 μm, made of PTFE). With respect to activated carbon on the filter, operation involving suspending the activated carbon in ethyl acetate of a weight 3 times as much as that of the crude product and washing the crude product by stirring the suspension for 10 minutes at 50° C. was repeated 5 times. Obtained filtrate and washing solution were mixed and after the ethyl acetate was removed in reduced pressure, the obtained product was heat-dried at 50° C. in vacuum to obtain a light yellow solid of Et$_3$MeNTCB (produced amount: 37 g (160 mmol), yield: 80%, melting point: 115° C.).

<Oxidizing Agent Treatment>

The obtained Et$_3$MeNTCB and hydrogen peroxide (aqueous 30 wt % H$_2$O$_2$ solution) in a weight 2.25 time as much as that of Et$_3$MeNTCB were added to a beaker equipped with a stirring device and a reflux condenser, and stirred for 60 minutes at 50° C.

<Extraction Treatment>

Next, butyl acetate in a weight 9 times as much as that of Et$_3$MeNTCB, which had been subjected to the activated carbon treatment, was added to the H$_2$O$_2$ solution of Et$_3$MeNTCB and the mixed solution was stirred. Thereafter, the mixed solution was transferred to a container (capacity: 1000 mL) for centrifugal separation and then the container was shaken for 90 seconds and subjected to centrifugal separation (1700 rpm, 10 minutes). The obtained butyl acetate layer (supernatant, an organic layer) was concentrated.

<Dry>

The butyl acetate layer containing Et$_3$MeNTCB which was obtained by the extraction treatment was further heated for 30 minutes (80° C.) in reduced pressure and the coarsely dried Et$_3$MeNTCB was pulverized with a mortar to obtain a powder. The obtained powder was spread on a tray on which a Teflon (registered trade name) sheet was spread and set in a vacuum drier and dried for 3 days at 80° C. in reduced pressure.

The NMR analysis results of the obtained Et$_3$MeNTCB are shown below. The ion component amounts in Et$_3$MeNTCB measured by the above-mentioned method are shown in Table 1. The product showed an NMR spectrum same as that of Synthesis Example 1-4.

Synthesis Example 5-2

The same operation as that of Synthesis Example 5-1 was carried out except that, in the oxidizing agent treatment, 83 mL of an aqueous. 30 weight % sodium perchlorate solution was used in place of hydrogen peroxide solution to synthesize Et$_3$MeNTCB.

Synthesis Example 5-3

Et$_3$MeNTCB was synthesized in the same manner as that in Synthesis Example 5-1, except that no activated carbon treatment was carried out after the synthesis of cude product.

Synthesis Example 5-4

Et$_3$MeNTCB synthesized in Synthesis Example 5-1 after the activated carbon treatment was used as a measurement sample.

Synthesis Example 5-5

Et$_3$MeNTCB in amount of 46 g produced in Synthesis Example 5-1 before the activated carbon treatment was mixed with 104 ml of aqueous 0.01 mol/L NaOH solution and stirred for 60 minutes at 50° C. Next, butyl acetate in a weight 9 times as much as that of Et$_3$MeNTCB was added to the NaOH solution of Et$_3$MeNTCB and extraction treatment was carried out in the same manner as in Synthesis Example 5-1 to synthesize Et$_3$MeNTCB (without activated carbon treatment and oxidizing agent treatment).

Synthesis Example 6

Synthesis Example 6-1

Tetrabutylammonium tetracyanoborate synthesis

As a product, a white solid tetrabutylammonium tetracyanoborate (Bu$_4$NTCB) was obtained by synthesis of a crude product and activated carbon treatment in the same manner as in Synthesis Example 5-1, except that 64.5 g (200 mmol) of tetrabutylammonium bromide was used in place of Et$_3$MeNCl used in Synthesis Example 5 (produced amount; 60.0 g (164 mmol), yield: 82%, melting point: 90° C.). The product showed an NMR spectrum same as that of Synthesis Example 1-1.

Synthesis Example 6-2

Bu$_4$NTCB obtained in Synthesis Example 6-1 was mixed with hydrogen peroxide solution (aqueous 30 wt % H$_2$O$_2$ solution) in a weight 2.25 times as much as that of Bu$_4$NTCB and stirred for 60 minutes at 50° C. Thereafter, extraction and drying treatment were carried out in the same manner as in Synthesis Example 5-1 to obtain a white solid of Bu$_4$NTCB. (produced amount; 45 g (120 mmol), yield: 62%).

Synthesis Example 7

Synthesis Example 7-1

1-Ethyl-3-Methylimidazolium Tetracyanoborate Synthesis

Synthesis of a crude product and activated carbon treatment were carried out in the same manner as in Synthesis Example 5-1, except that 38.2 g (200 mmol) of 1-ethyl-3-methylimidazolium bromide was used in place of Et$_3$MeNCl to obtain a light yellow oil of 1-ethyl-3-methylimidazolium tetracyanoborate (EtMeImTCB) as a product (produced amount; 24.9 g (110 mmol), yield: 55%, melting point: 15° C.). The product showed an NMR spectrum same as that of Synthesis Example 1-2.

Synthesis Example 7-2

EtMeImTCB obtained in Synthesis Example 7-1 was mixed with hydrogen peroxide solution (aqueous 30 wt % H$_2$O$_2$ solution) in a weight 2.25 times as much as that of EtMeImTCB and stirred for 60 minutes at 50° C. Thereafter, extraction and drying treatment were carried out in the same manner as in Experiment Example 1-1 to obtain a light yellow oil of EtMeImTCB (produced amount; 18 g (80 mmol), yield: 40%).

Synthesis Example 8

Synthesis Example 8-1

Triethylammonium Tetracyanoborate Synthesis

Synthesis of a crude product and activated carbon treatment were carried out in the same manner as in Synthesis Example 5-1, except that 20.2 g (200 mmol) of triethylamine was used in place of Et$_3$MeNCl to obtain a light yellow solid of triethylammonium tetracyanoborate (Et$_3$NHTCB) as a product (produced amount; 23.8 g (110 mmol), yield: 60%, melting point: 150° C. The product showed an NMR spectrum same as that of Synthesis Example 1-3.

Synthesis Example 8-2

Et$_3$NHTCB obtained in Synthesis Example 8-1 was mixed with hydrogen peroxide solution (aqueous 30 wt % H$_2$O$_2$ solution) in a weight 2.25 times as much as that of Et$_3$NHTCB and stirred for 60 minutes at 50° C. Thereafter, extraction and drying treatment were carried out in the same manner as in Synthesis Example 5-1 to obtain a light yellow solid of Et₃NHTCB (produced amount; 17 g (80 mmol), yield: 40%).

Synthesis Example 9

Synthesis Example 9-1

Tetraethylammonium Tetracyanoborate Synthesis

Synthesis of a crude product and activated carbon treatment were carried out in the same manner as in Synthesis Example 5-1, except that 33.1 g (200 mmol) of tetraethylammonium chloride was used in place of Et₃MeNCl to obtain a white solid of tetraethylammonium tetracyanoborate (Et₄NTCB) as a product (produced amount; 46.6 g (190 mmol), yield: 95%, melting point: 150° C.). The product showed an NMR spectrum same as that of Synthesis Example 1-5.

Synthesis Example 9-2

Et₄NTCB obtained in Synthesis Example 9-1 was mixed with hydrogen peroxide solution (aqueous 30 wt % H₂O₂ solution) in a weight 2.25 times as much as that of Et₄NTCB and stirred for 60 minutes at 50° C. Thereafter, extraction and drying treatment were carried out in the same manner as in Synthesis Example 5-1 to obtain a light yellow solid of Et₄NTCB (produced amount; 35 g (144 mmol), yield: 72%).

Synthesis Example 10

Synthesis Example 10-1

Tetramethylammonium Tetracyanoborate Synthesis

Synthesis of a crude product and activated carbon treatment were carried out in the same manner as in Synthesis Example 5-1, except that 21.9 g (200 mmol) of tetramethylammonium chloride was used in place of Et₃MeNCl to obtain a white solid of tetramethylammonium tetracyanoborate (Me₄NTCB) as a product (produced amount; 26.5 g (140 mmol), yield: 70%).
¹H-NMR(d6-DMSO) δ 3.08(s, 12H)
¹³C-NMR(d6-DMSO) δ 121.9(m),55.3(s)
¹¹B—NMR(d6-DMSO) δ −39.6(s)

Synthesis Example 10-2

Me₄NTCB obtained in Synthesis Example 10-1 was mixed with hydrogen peroxide solution (aqueous 30 wt % H₂O₂ solution) in a weight 2.25 times as much as that of Me₄NTCB and stirred for 60 minutes at 50° C. Thereafter, extraction and drying treatment were carried out in the same manner as in Synthesis Example 5-1 to obtain a light yellow solid of Me₄NTCB (produced amount; 11 g (100 mmol), yield: 50%).

Synthesis Example 11

Synthesis Example 11-1

Tributylmethylammonium Tetracyanoborate Synthesis

Synthesis of a crude product and activated carbon treatment were carried out in the same manner as in Synthesis Example 5-1 except that 44.4 g (200 mmol) of tributylammonium chloride was used in place of Et₃MeNCl to obtain a yellow solid of tributylammonium tetracyanoborate (Bu₃NHTCB) as a product (produced amount; 48.2 g (160 mmol), yield: 80%). The product showed an NMR spectrum same as that of Synthesis Example 3-16.

Synthesis Example 11-2

Bu₃NHTCB obtained in Synthesis Example 11-1 was mixed with hydrogen peroxide solution (aqueous 30 wt % H₂O₂ solution) in a weight 2.25 times as much as that of Bu₃NHTCB and stirred for 60 minutes at 50° C. Thereafter, extraction and drying treatment were carried out in the same manner as in Synthesis Example 5-1 to obtain a yellow solid of Bu₃NHTCB (produced amount; 39 g (0.13 mmol), yield: 65%).

The various kinds of ion components contained in each ionic compound produced in Synthesis Examples 5 to 11 were measured by the above-mentioned methods. The results are shown in Table 3. In Table 3, "N.D." showed that the amount of an impure ion component contained in a measurement sample was measurement limit (1 ppm) or lower.

TABLE 3

| | Treatment | | | | | | | | |
|---|---|---|---|---|---|---|---|---|---|
| | Activated carbon | Oxidizing agent | Extraction | Cl/ppm | Br/ppm | CN/ppm | Na/ppm | Si/ppm | Water/ppm |
| Synthesis Example 5-1 | employed | H₂O₂ | employed | 4 | — | 288 | N.D. | N.D. | 83 |
| Synthesis Example 5-2 | employed | NaClO₄ | employed | 94 | — | 10 | 1180 | 131 | 110 |
| Synthesis Example 5-3 | not employed | H₂O₂ | employed | <1 | — | 119 | 40 | 31 | 114 |
| Synthesis Example 5-4 | employed | not employed | not employed | 350 | — | 6700 | 32 | 22000 | 1750 |
| Synthesis Example 5-5 | employed | H₂O₂ | NaOH extraction | 86 | — | 550 | 744 | 2724 | 530 |
| Synthesis Example 6-1 | employed | not employed | not employed | 570 | — | 1600 | 32 | 16900 | 1840 |

TABLE 3-continued

| | Treatment | | | | | | | | |
|---|---|---|---|---|---|---|---|---|---|
| | Activated carbon | Oxidizing agent | Extraction | Cl/ppm | Br/ppm | CN/ppm | Na/ppm | Si/ppm | Water/ppm |
| Synthesis Example 6-2 | employed | $H_2O_2$ | employed | 3 | — | 161 | 9 | 236 | 80 |
| Synthesis Example 7-1 | employed | not employed | not employed | 630 | 480 | 2990 | 5 | 50300 | 1620 |
| Synthesis Example 7-2 | employed | $H_2O_2$ | employed | 5 | <1 | 86 | 10 | 6 | 83 |
| Synthesis Example 8-1 | employed | not employed | not employed | 439 | — | 152 | 192 | 28200 | 3200 |
| Synthesis Example 8-2 | employed | $H_2O_2$ | employed | <1 | — | 110 | N.D. | 12 | 66 |
| Synthesis Example 9-1 | employed | not employed | not employed | 1210 | — | 6740 | 9 | 3000 | 4800 |
| Synthesis Example 9-2 | employed | $H_2O_2$ | employed | <1 | — | 119 | 39 | 31 | 114 |
| Synthesis Example 10-1 | employed | not employed | not employed | 2300 | — | 4320 | 8 | 42100 | 2200 |
| Synthesis Example 10-2 | employed | $H_2O_2$ | employed | 4 | — | 288 | N.D. | N.D. | N.D. |
| Synthesis Example 11-1 | employed | not employed | not employed | 3200 | — | 3420 | 21 | 19800 | 2400 |
| Synthesis Example 11-2 | employed | $H_2O_2$ | employed | 5 | — | 268 | 8 | 18 | 100 |

From the results of Synthesis Examples 5 to 11, it can be understood that Si, cyanide ion ($CN^-$), and halide ion ($Cl^-$ or $Br^-$) remaining in the ionic compound are decreased by the oxidizing agent treatment by bringing the ionic compound into contact with an oxidizing agent.

Further, from the results of Synthesis Example 5, it can be understood that the effect of the oxidizing agent treatment became furthermore efficient by combination with activated carbon treatment and extraction treatment (comparison of Synthesis Example 5-1 and Synthesis Example 5-3) and furthermore, it can also be understood that the water content in the ionic compound are further decreased in the case hydrogen peroxide is used as an oxidizing agent by comparing Synthesis Example 5-1 and Synthesis Example 5-2.

That is, according to the invention, a high purity ionic compound with decreased content of impure ions which are contained in the starting materials and are inevitably mixed during production is obtained.

Example 6

In Example 6, the highest occupied molecular orbital energy level of various kind of anions having a structure defined by the general formula $[(NC)_v-X^{d-}]$ was calculated (Experiment Example 5) and the withstand voltage range LSV of actually synthesized anions was measured (Experiment Example 6).

Experiment Example 5

Calculation of Highest Occupied Molecular Orbital Energy Level

Calculation of the highest occupied molecular orbital energy level of various kinds of anions shown in Table 4 below was carried out, employing GAUSSIAN 03 (manufactured by GAUSSIAN, Inc.) and using B3LYP/6-311+G(2d, p) for the basis function. The calculation results of the highest occupied molecular orbital energy level are shown in Table 4.

TABLE 4

| No | Anion | Energy level [eV] |
|---|---|---|
| 1 | OCN | −0.856 |
| 2 | SCN | −1.082 |
| 3 | $N(CN)_2$ | −1.776 |
| 4 | $C(CN)_2$ | −1.983 |
| 5 | $Se(CN)_3$ | −3.745 |
| 6 | $B(CN)_4$ | −5.809 |
| 7 | $Al(CN)_4$ | −6.107 |
| 8 | $Ga(CN)_4$ | −6.077 |
| 9 | $Si(CN)_5$ | −5.961 |
| 10 | $Ge(CN)_5$ | −5.735 |
| 11 | $P(CN)_6$ | −6.561 |
| 12 | $As(CN)_6$ | −6.744 |
| 13 | $B(CN)_3F$ | −5.421 |
| 14 | $B(CN)_2F_2$ | −4.974 |
| 15 | $B(CN)F_3$ | −4.642 |
| 16 | $BF_4$ | −4.499 |
| 17 | $PF_6$ | −5.319 |
| 18 | $AsF_6$ | −5.862 |

Experiment Example 6

Linear Sweep Voltammetry (LSV Measurement)

In Experiment Example 6, withstand voltage range LSV of actually synthesized anions was measured. LSV measurement was carried out as follows.

[Measurement of Withstand Voltage Range LSV]

The withstand voltage range was measured by carrying out LSV measurement by a standard voltammetry tool HSV-100 (trade name, manufactured by Hokuto Denko Corporation) using a tripolar cell in a glove box at 30° C. atmosphere. The measurement conditions are as follows.

(Measurement Condition)

Working electrode: Glassy carbon electrode, Reference electrode; Ag electrode, counter electrode: Platinum electrode Solution concentration: 1 mol/L
Solvent: propylene carbonate
Sweeping speed: 100 mV/s
Sweeping range: spontaneous potential to ±5V Experiment Example 6-1

Et$_3$MeNTCB obtained in Synthesis Example 1-3 was dissolved in dehydrated propylene carbonate (manufactured by Kishida Chemical Co., Ltd.) to have a concentration of 1 mol/L and subjected to LSV measurement. The result is shown in FIG. 1.

Experiment Example 6-2

Figure 2:
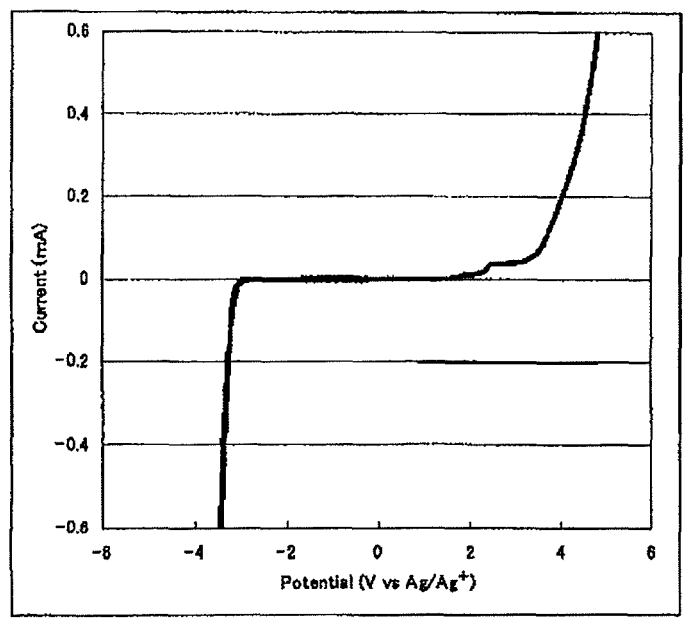
FIG. 2. A drawing showing LSV measurement result of Experiment Example 6-2.

A 2.0 mol/LPC solution of commercialized triethylmethylammonium tetrafluoroborate (TEMABF$_4$) (manufactured by Kishida Chemical Co., Ltd.) was diluted to 1.0 mol/L and then subjected to LSV measurement. The result is shown in FIG. 2.

In Table 4, the anions shown in No. 6 to 11 had the highest occupied molecular orbital energy level lower than −5.5 eV and it is implied that the anions had wide potential window. Actually, as shown in Experiment Example 6-1 (FIG. 1), although slight electric current was observed around 2 V, electric current in Et$_3$MeNTCB having the HOMO level of −5.809 eV was scarcely observed in a voltage range higher than that and thus it can be understood that Et$_3$MeNTCB is a compound having a wider withstand voltage range than Et$_3$MeNBF$_4$ shown in Experiment Example 6-2 (FIG. 2).

Since an ion-conductive material of the invention has a wide potential window and contains no harmful substance such as F and As, it can be used preferably for uses such as lithium ion batteries, lithium ion capacitors, electric double layer capacitors, and electrolytic capacitors.

Industrial Applicability

An ionic compound containing tetracyanoborate obtained by the production method of the invention is used preferably for various uses as constituent materials of various kinds of electrochemical devices such as ion conductors (electrolytic solution materials or the like), e.g., lithium secondary batteries, electrolytic capacitors, electric double layer capacitors, lithium ion capacitors, etc., a reaction solvent for organic synthesis, a conductivity supply agent for polymers, a lubricant, a gas absorbent, etc.

Especially, if an ionic compound of the invention is used, a highly reliably electrolyte solution material and an additive such as a conductivity supply agent and a lubricant is provided.

The invention claimed is:

1. A method for producing an ionic compound represented by formula (I), comprising a step of reacting starting materials containing trimethylsilyl cyanide, a boron compound, and an amine and/or ammonium salt,
   wherein the boron compound is at least one selected from the group consisting of M$^c$BX$^c_4$, BX$^c_3$, BX$^c_3$-complex, and B(OR$^{13}$)$_3$,
   wherein M$^c$ denotes a hydrogen atom or an alkali metal atom, X$^c$ denotes a hydrogen atom, a hydroxyl group or a halogen atom, and R$^{13}$ denotes a hydrogen atom or an alkyl group:

(I)

wherein Kt$^{m+}$ denotes an ammonium cation, and m denotes an integer of 1.

2. The method for producing an ionic compound according to claim 1, wherein the starting materials contain ammonium salt.

3. The method for producing an ionic compound according to claim 2, wherein the ammonium salt contains a halide ion as an anion.

4. The method for producing an ionic compound according to claim 1, wherein the ammonium salt contains a halide ion as an anion.

5. The method for producing an ionic compound according to claim 1, further comprising a step of bringing a crude product obtained by reacting the starting materials into contact with an oxidizing agent.

6. The method for producing an ionic compound according to claim 5, wherein the oxidizing agent is hydrogen peroxide.

7. A method for producing an ionic compound containing an alkali metal cation, comprising reacting starting materials containing trimethylsilyl cyanide, a boron compound, and an amine and/or ammonium salt to produce an ionic compound represented by formula (I),
   wherein the boron compound is at least one selected from the group consisting of M$^c$BX$^c_4$, BX$^c_3$, BX$^c_3$-complex, and B(OR$^{13}$)$_3$,
   wherein M$^c$ denotes a hydrogen atom or an alkali metal atom, X$^c$ denotes a hydrogen atom, a hydroxyl group or a halogen atom, and R$^{13}$ denotes a hydrogen atom or an alkyl group:

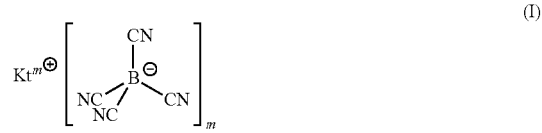

(I)

wherein Kt$^{m+}$ denotes an ammonium cation, and m denotes an integer of 1, and
carrying out a cation exchange reaction, wherein the ammonium cation contained in the ionic compound represented by formula (I) is exchanged for the alkali metal cation.

* * * * *